(12) United States Patent
Bursavich et al.

(10) Patent No.: US 6,947,847 B2
(45) Date of Patent: Sep. 20, 2005

(54) METHOD TO DESIGN THERAPEUTICALLY IMPORTANT COMPOUNDS

(75) Inventors: Matthew G. Bursavich, Madison, WI (US); Daniel H. Rich, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 360 days.

(21) Appl. No.: 10/094,049

(22) Filed: Mar. 8, 2002

(65) Prior Publication Data

US 2003/0190670 A1 Oct. 9, 2003

(51) Int. Cl.[7] ............................ G01N 33/48; G06G 7/60
(52) U.S. Cl. ........................................... 702/27; 703/11
(58) Field of Search ............................... 702/27; 703/11

(56) References Cited

FOREIGN PATENT DOCUMENTS

WO    WO 02/088101 A2    11/2002

OTHER PUBLICATIONS

Carlson et al. Accommadating Protein Flexibility in Computational Drug Design. Mol. Pharmacol. vol. 57, pp. 213–281, (2000).*
Abad–Zapatero et al. (1990) *Proteins: Struct., Funct., Genet.* 8:62–81.
Babine & Bender (1997) *Chem. Rev.* 97:1359–1472.
Bohacek & McMartin (1992) *J. Med. Chem.* 35:1671–1684.
Bohacek & McMartin (1994) *J. Am. Chem. Soc.* 116:5560–5571.
Bohacek, McMartin, & Guida (1996) *Med Res. Rev.* 16(1):3–50.
Böhm (1992) "LUDI: rule–based automatic design of new substituents for enzyme inhibitor leads," *J. Comp.–Aided Mol. Des.* 6:593–606.
Böhm (1992) "The computer program LUDI: a new method for the de novo design of enzyme inhibitors," *J. Comp.–Aided Mol. Des.* 6:61–78.
Bursavich, West, & Rich (2001) *Org. Lett.* 3(15):2317–2320.
Carter & Wells (1987) *Science* 237:394–399.
Clackson & Wells (1995) *Science* 267:383–386.
DeLucca et al. (1997) *Drug Discov. Today* 2: 6–18.
Eisen et al. (1994) "Hook: A program for finding novel molecular architectures that satisfy the chemical and steric requirements of a macromolecule binding site," *Proteins: Struct., Funct., Genet.* 19:199–221.
Farmer, "Bridging the gap between bioactive peptides and nonpeptides: some perspectives in design," in *Drug Design;* Ariens, E. J., Ed.; Academic Press: New York; vol. 10, pp. 119–143 (1980).
Flentke et al. (1999) *Protein Expression & Purif.* 16:213–220.
Fletcher & Campbell (1998) *Chem. Rev.* 98:763–795.
Gillet et al. (1995) "Sprout, Hippo and CAESA: tools for de novo structure generation and estimation of synthetic accessibility," *Perspect. In Drug Discovery & Des.* 3:34–50.
Gilliland et al. (1990) *Proteins: Struct., Funct., Genet.* 8:82–101.
Goodfod, P. J. (1985) *J. Med. Chem.* 28:849–857.
Groves et al. (1998) *Protein Eng.* 11(10):833–840.
Güller et al. (1999) *Bioorg. & Med. Chem. Lett.* 9:1403–1408.
Hart & Rich, "Stereochemical aspects of drug action I: Conformational restriction, steric hindrance and hydrophobic collapse," in *Pract. Of Med. Chem.;* Wermuth, C., Ed.; Acad. Press: London, UK, 1996; pp. 393–412.
Hellinga & Richards (1991) *J. Mol. Biol.* 222:763–785.
Hellinga, Caradonna, & Richards (1991) *J. Mol. Biol.* 222:787–803.
Ho & Marshall (1993) "Splice: a program to assemble partial query solutions from three–dimensional database searches into novel ligands," *J. Comput.–Aided Mol. Des.* 7:623–647.
Inooka et al. (2001) *Nature Structural Biology* 8(2):161–165.
James, Hsu, & Delabaere (1977) *Nature* 267:808–813.
James et al. (1982) *Proc. Natl. Acad. Sci. U. S. A.* 79:6137–6141.
James & Sielecki (1983) *J. Mol. Biol.* 163:299–361.
Koshland (1958) *Proc. Natl. Acad. Sci. U. S. A.* 44:98–104.
Kumar et al. (1999) *Cell Biochem. and Biophys.* 31:141–164.
Lam et al. (1996) *J. Med. Chem.* 39:3514–3525.
Lauri & Bartlett (1994) "Caveat: a program to facilitate the design of organic molecules," *J. of Comput.–Aided Mol. Des.* 8:51–66.
Lebon & Ledocq (2000) *Curr. Med. Chem.* 7:455–477.
Lien, Gao, & Lien (1994) *Progress in Drug Research* 43:43–86.
Ma et al. (1999) *Proteins Eng.* 12:713–720.
Märki et al. (2001) *Il Farmaco* 56:21–27.
Martin et al. (1999) *Biochemistry* 38:7978–7988.
Moon & Howe (1991) "Computer design of bioactive molecules: a method for receptor–based de novo ligand design," *Proteins* 11:314–328.

(Continued)

*Primary Examiner*—John S. Brusca
(74) *Attorney, Agent, or Firm*—Joseph T. Leone, Esq.; DeWitt Ross & Stevens S.C.

(57) ABSTRACT

Disclosed is are methods of generating chemical structures of putative non-peptide inhibitors of biologically-active receptors. The method includes constructing a model of a receptor-ligand complex using empirical three-dimensional data of the receptor-ligand complex. The conformation of the binding site between the receptor and the ligand is then altered to yield novel conformations not exhibited in either the native receptor or the bound receptor. These conformations are then used to generate models of non-peptide chemical structures that are complementary in structure to the altered conformations of the binding site. In this fashion, chemical structures of putative non-peptide inhibitors of the altered conformation are revealed.

13 Claims, No Drawings

OTHER PUBLICATIONS

Newman et al.(1991) *J. Mol. Biol.* 221:1295–1309.
Nishibata & Itai (1991) *Tetrahedron* 47(43):8985–8990.
Northrop (2001) *Acc. Chem. Res.* 34:790–797.
Oefner et al. (1999) *Chem. & Biol.* 6:127–131.
Olson et al. (1993) *J. of Med. Chem.* 36(21):3039–3049.
Piana et al. (2001) *J. Am. Chem. Soc.* 123:8730–8737.
Peranteau et al. (1995) *Anal. Biochem.* 227:242–245.
Rahuel, J., et al. (2000) *Chem. Biol.* 7:493–504.
Rich et al. (1991). *J. Med. Chem.* 34:1222–1225.
Rich et al., in *Medicinal Chemistry into the Millennium;* Campbell, M. M., Blagbrough, I. S., Eds.; Royal Society of Chemistry, Publ.: Cambridge UK, 2001; pp 16–24.
Ripka & Rich (1998) *Curr. Op. in Chem. Biol.* 2:441–452.
Rotstein & Murcko (1993) "GroupBuild: a fragment–based method for de novo drug design," *J. Med. Chem.* 36:1700–1710.
Rotstein & Murcko (1993) *J. of Comput.–Aided Mol. Des.* 7:23–43.
Singh, Saldanha, & Thornton (1991) "A novel method for the modeling of peptid ligands to their receptors," *Protein Eng.* 4(3):251–261.
Sowdhamini et al. (1995) *Pharm. Acta Helv.* 69:185–192.
Spatola, "Peptide backbone modifications; a structure–activity analysis of peptides containing amide bond surrogates, conformational constraints, and related backbone replacements" in *Chem. Biochem. Amino Acids, Pept., Proteins;* Weinstein, B., Ed.; Marcel Dekker, Inc: New York, 1983; pp. 267–357.
Straub (1964) *Advan. Enzymol.* 26:89–114.

\* cited by examiner

METHOD TO DESIGN THERAPEUTICALLY IMPORTANT COMPOUNDS

FIELD OF THE INVENTION

The invention is directed to a method of designing non-peptide compounds that are biologically active inhibitors of a pre-determined target receptor, such as an enzyme or receptor. The method probes conformational ensembles of a targeted receptor/ligand complex to reveal novel conformations within the receptor binding site. These conformations are unobserved in the unoccupied enzyme or receptor. Knowledge of these conformations enables the rational design of non-peptide peptidomimetic compounds to interact with these conformations of the targeted receptor, thus aiding in the discovery of novel, biologically-active compounds.

BACKGROUND

Since roughly 1980, advances in computer technology, both hardware and software, and new techniques and advancements in chemistry and biology, have added additional levels of sophistication to the research done in biotechnology, drug discovery, and biomedical research. Many of the techniques developed are computational in nature. The vast increase in computational power and speed enables biological systems to be modeled, analyzed, and altered in great detail. The results of such computational modeling can then be utilized to design new drugs on a rational basis. This field of computational biological and chemical research is referred to herein as research done in silico. The adjective "in silico" thus refers to biochemical research wherein the system under investigation is mathematically modeled, modified, altered, and otherwise studied entirely within a computer-generated algorithmic model. The programming of the computer is based upon empirical knowledge of a host of chemical and physical parameters, such as three-dimensional geometry, bond lengths, bond strength, torsion, rotation, steric and electronic interactions, etc. In short, the amount of empirical biochemical data gathered to date greatly outstrips the conventional chemical and biochemical means of evaluating the significance of the collected data. "In silico" research thus designates the exploration and analysis of large quantities of empirical data by automatic and/or semi-automatic means in order to discover meaningful and predictive patterns and rules governing biological systems. The automatic and/or semi-automatic means for performing such research generally takes the form of a programmable computer and the input of the human programmer.

Traditionally, new drugs were found by isolating a molecule with a certain biological activity. This lead compound was then chemically modified using clues provided by a crude analysis of structure-activity relationships or by traditional medicinal chemistry techniques. The new, modified compounds were then synthesized and re-screened for the desired biological activity. This cycle continued until the desired biological activity of the compound was maximized. This approach, while effective, is very, very slow. A period of five or six years to bring a new drug to the preclinical phase is not uncommon using this traditional approach to drug discovery.

The in silico approach recognizes that many drugs are inhibitors of macromolecules (most often a protein, such as an enzyme or a proteinaceous receptor). Thus, a target molecule is chosen a priori, before any actual experiments are begun. The biological target is a macromolecule which is believed to be, or known to be, crucial for the biological activity or process which is to be inhibited. Of course, selecting a target for investigation is not always a simple process, especially when the biological activity to be inhibited is not parasitic in nature or when the number of possible targets is enormous.

Once a target has been selected, however, several technologies conventionally come into play using the in silico approach. As a general rule, the macromolecule to be studied is purified. An initial lead compound is then discovered by a variety of techniques such as high-throughput screening, where hundreds of thousands of compounds are examined en masse for binding to the purified target. Often, in a concurrent effort, the three-dimensional structure of the target macromolecule may be determined using nuclear magnetic resonance (NMR), X-ray crystallography, and other molecular modeling techniques. This data is collated and is used in designing the next series of compounds, which are then synthesized. This cycle is repeated until a compound is sufficiently potent, at which point it is sent to preclinical testing (on animals) and clinical testing (on humans). While faster that the conventional SAR aproach, in the current discovery cycle, an average time to reach preclinical investigation is still roughly three years.

Computer modeling of a biological system, of course, requires a good deal of empirical data, as well as theoretical models of macromolecular interactions. During the past 100 years, ligand binding has been described via two basic rationales. Emil Fisher first proposed in 1894 the "lock and key" rationale to describe ligand-receptor binding. Fischer (1894) Ber. dt. chem. Ges. 27:2985. In this model, the receptor (as used herein, the term "receptor" explicitly includes enzymes of all description, including ribozymes) is symbolized by a rigid lock into which the symbolic key, or ligand, must precisely fit. This was the sole model used to describe ligand binding events for over 50 years. In 1958, Koshland proposed an "induced fit" model to describe ligand-receptor binding events that seemed to proceed in a zipper-like fashion. Koshland (1958) Proc. Natl. Acad. Sci. U.S.A. 44:98. He hypothesized that binding of the substrate "causes a change in the 3-dimensional relationship in the active site." It is this change that then leads to a fit that occurs only after the changes induced by ligand binding. Over the years, conformational changes of the receptor ascribed to an "induced fit" binding have ranged from very subtle movements of amino acid side chains to large conformational changes involving movements of entire protein domains.

These two complementary models have been utilized to describe most of the structural data presently available in the literature. The "lock and key" rationale describes the binding event if, after inspection of the ligand-receptor complex, the observed receptor conformation resembles the unbound-receptor conformation. Conversely, if the conformation of the bound-receptor is different than the unbound-receptor (no matter how subtle the differences), then the "induced fit" model rationalizes the observed ligand-binding process.

Recently, "stabilization of receptor conformational ensembles" has emerged to rationalize a range of ligand binding events without necessitating either the "lock and key" or "induced fit" mechanisms. See Kumar et al. (1999) Cell Biochem. and Biophys. 31:141–164; Ma et al. (1999) Protein Eng. 12:713–720; Tsai et al. (1999) Protein Sci. 8:1181–1190. This model assumes that macromolecules exist in solution as multiple, equilibrating conformations.

These various conformations can be described by mechanical laws, using standard statistical distributions. The process of ligands binding to the receptors thus shifts the equilibrium from the statistical distribution of native conformations when the ligand is absent, to a new equilibrium that includes the receptor-ligand conformation. In this view, ligands bind to an ensemble of pre-existing receptor conformations. Ligand binding then shifts the overall dynamic equilibrium to stabilize the conformation present in the receptor-ligand complex.

This concept of conformationally mobile receptors (and ligands) is not new, but arose shortly after the discovery of modern conformational analysis. A paper published in 1964 states that "the conformation of an enzyme in solution is regarded to be a statistical average of a number of conformations, the protein structure oscillating between these conformations." Straub (1964) *Advan. Enzymol.* 26:89–114. Since then, the conformational mobility of biologically active proteins has been repeatedly demonstrated via biophysical methods.

Nevertheless, due to computational limitations, current molecular modeling and drug design efforts treat proteins as static models even though they are clearly dynamic macromolecular structures, constantly in motion. In general, the static models portray either the native protein conformation or the protein conformation tightly bound to a potent peptide-derived inhibitor. Some modeling studies accommodate small changes in protein and ligand side chain conformations or hydrogen bonding interactions. This approach, called the "soft lock and key" model has subsequently been utilized to modify inhibitor design. Sowdhamini et al. (1995) *Pharm. Acta Helv.* 69:185–192.

But other (and significantly altered) protein conformations are not considered when designing or modifying enzyme inhibitors, in spite of the fact that biophysical methods have established their existence. Thus, there remains a long-felt and unmet need to explore these conformations as a means to yield information that leads to the rational design of targeted, biologically-active compounds.

SUMMARY OF THE INVENTION

A major goal in developing novel pharmaceuticals is to find new, biologically-active compounds that have desirable pharmacodynamic properties, exhibit those properties when taken orally, have a sufficiently long duration of action to minimize the number of daily doses required, exhibit little or no side-effects, etc. Achieving this goal in an efficient manner requires that potential drug candidates be designed rationally, with a targeted receptor in mind from the outset. According to the present invention, designing structurally novel inhibitors requires targeting receptor conformations located outside the narrow window of conformational ensembles conventionally exploited via current inhibitors. In short, the present invention is a method of systematically exploring novel receptor conformations that are unobserved in either the native receptor or receptor-ligand complexes as a means to design novel drugs on a rational basis.

The method of the present invention utilizes currently available computer modeling programs to model receptor conformations based upon the three-dimensional data of a given receptor-ligand or receptor-inhibitor complex. In short, the three-dimensional data for a receptor-ligand complex is used first to construct a mathematical model of the geometry and chemistry of the binding site within the receptor-ligand complex. In a first embodiment of the invention, the ligand portion of the model is then mathematically excised from the receptor binding site portion of the model, again using any number of commercially-available chemical structure modeling programs. The now-unoccupied binding site conformation is thus mathematically modeled. Note, however, that the model does not depict the native receptor binding site; the model depicts the binding site as it appears when the ligand is bound. This is the target that is conventionally utilized in rational drug design.

In the present invention, however, this model target conformation is then systematically altered (preferably using Monte Carlo methods) to yield novel conformational models. These altered models thus define an ensemble of previously unobserved active site conformations. Some of the individual conformations within the ensemble will be related to chemically rational and reasonable catalytic/mechanistic intermediates. Other conformations within the ensemble may be completely unanticipated. But none of the conformations within the ensemble will have been observed previously. Of course, because none of these model conformations have been previously observed, they likewise have never been investigated as active sites in the rational design of a corresponding inhibitor for such a conformation. It is these novel active site conformations that are generated and utilized in the present invention to provide additional information for rational drug design. In short, the present invention provides a means or a strategy for systematically altering the conformation of an occupied binding site to thereby identify novel binding site conformations not observable in either the native enzyme or an enzyme-substrate or enzyme-inhibitor complex. Potential inhibitors can then be generated on a rational basis to fit these novel, altered conformations.

This is a critical difference between the conventional approaches to rational drug design and the present invention. Modeling the native receptor itself (i.e., modeling the unoccupied receptor based upon three-dimensional data of the native receptor) or the receptor-ligand complex does not reveal other conformations of the binding site when binding has taken place. This is because the act of binding itself changes the conformation of the binding site (and potentially other sites on the receptor). This happens so fast, and potentially in concerted action, that these changes are not observable. The process of binding cannot be stopped or slowed to reveal these unobserved conformations. As noted above, the changes that occur upon binding might be slight or they might be prodigious. In the final analysis, however, conformational changes in the binding site (and likely elsewhere in the receptor) do take place upon the binding of a ligand to the receptor. The present invention models plausible and novel alterations to the bindings site to reveal chemical structures that are likely to act as inhibitors of the receptor.

With the mathematical model of the conformation of the binding site in hand, the receptor site conformation is then altered systematically (again using commercially available chemical structure programs) by modifying such parameters as bond length, bond angles, bond torsion energy, total energy, spatial and steric interactions, electrostatic interactions, etc. This data is then utilized to model, in silico and on a rational basis, combinatorial libraries of compounds whose composition and structure will complement more closely the geometry and chemistry of the mathematically-generated, novel altered binding site conformations.

While not being limited to a particular mechanism of action, there is strong evidence that unoccupied receptors do exist in solution as ensembles of dynamically equilibrating conformations. Thus, by constructing potential inhibitors based upon models of altered receptor site conformations, those compounds whose size, geometry, and chemistry make them clearly unsuitable as inhibitors for a chosen target can be eliminated from consideration prior to actual screening.

An apt analogy to illustrate both the prior art and the present invention is to consider modeling the conformation of a baseball catcher's mitt (the receptor) in an effort to determine the proper size and shape of a baseball substitute (the inhibitor to be rationally designed). When unoccupied, the pocket of a catcher's mitt takes the form of a rather large, shapeless cup. However, when the catcher fields a pitched baseball, the force of the incoming ball, coupled with the closing force of the catcher's hand within the mitt, wraps the mitt securely around the ball, trapping the ball within. In this conformation, with the ball safely ensconced within the mitt, the pocket of the mitt looks vastly different. Rather than a shapeless cup, the pocket of the mitt now resembles a tight, encircling cavity. The conventional, prior art, approach is to "remove" the ball from the mitt, without opening the catcher's gloved hand. In this fashion, knowledge about the interior dimensions of the pocket can be gathered, dimensions that are totally different when the mitt is physically empty.

The end result in the conventional approach is that the physical dimensions of the pocket of the mitt, when occupied by the baseball, mirror the physical dimensions of the baseball itself. Armed with that knowledge, rational predictions can now be made regarding whether balls having different dimensions can be made to fit within the structure of the occupied pocket or an altered conformation of the occupied pocket. Continuing with the catcher's mitt analogy, the conventional approach then resorts to a computational analysis of the model to predict that no, a football (either an American-style football or a soccer ball) will not fit within the pocket of the catcher's mitt or any plausible conformation of the pocket. The American-style football simply is too big and too oddly shaped to complement the observed geometry of the mitt. The soccer ball, while spherical like a baseball, has too large a diameter to fit within the mitt. Similarly, a golf ball or a ping-pong ball, while also spherical like a baseball, is an unlikely candidate because each is too small in diameter. A tennis ball, however, is a good candidate, as is a lacrosse ball. Both are spherical and approximately the same diameter as a baseball. Thus it can be predicted a priori (i.e., without any previous knowledge of what a tennis ball or lacrosse ball looks like) that a ball shaped like a tennis ball or a lacrosse ball will fit within the pocket and thus is a good candidate for further empirical investigation.

The present invention, however, is distinctly different because the inventors have discovered that the shape of the catcher's mitt (i.e., the conformation of enzyme or receptor) can be altered in unanticipated and unobservable fashion. Thus, continuing the analogy, it is as if the inventors have discovered (quite surprisingly and contrary to common practice and scientifically-accepted belief) that the thumb of the catcher's mitt is fully opposable. Thus, the thumb of the mitt can be made to fold in such a fashion as to cover the pocket of the mitt completely. In this conformation, not even the baseball itself can enter the mitt (nor the tennis ball, nor the lacrosse ball). But, other shapes can be found that will fit this new and previously unknown conformation. For example, a C-shaped or U-shaped "ball" would fit into the pocket now blocked by the opposable thumb portion of the mitt. In this analogy, the thumb would rest in the concave portion of the C-shaped or U-shaped ball, and the convex portion of the ball would rest within the pocket of the mitt. Further analysis might reveal that a V-shaped "ball" or a G-shaped "ball" will also fit into this partially-blocked conformation.

In short, in the present invention, the initial model of the receptor-ligand complex is altered systematically, using empirically-derived chemical and physical parameters, to arrive at other conformations of the active site (i.e., the shape of the pocket of the mitt) that might can be inhibited by novel chemical structures (i.e., balls whose shape is very, very different from that of a baseball).

The method requires that three-dimensional data of the receptor-ligand or receptor-inhibitor complex be acquired or already at hand. How this data is acquired is not critical to the functionality of the invention. All that is required is that there be three-dimensional data on the structure of the receptor-ligand complex under investigation. It is this data that is used to generate a model of the structure of the binding site and to generate plausible and novel permutations of the model.

Thus, a first embodiment of the invention is directed to a method of generating chemical structures of putative non-peptide inhibitors of a biologically-active receptor. The method comprises first constructing a model of a receptor-ligand complex using empirical three-dimensional data of the receptor-ligand complex, the model including a receptor portion and a ligand portion, whereby a conformation of a binding site between the receptor portion of the model and the ligand portion of the model is revealed. Then, the conformation of the binding site is altered to yield a model of an altered and novel conformation of the binding site. Then models of non-peptide chemical structures are generated that are complementary in structure to the altered conformation of the binding site. In this fashion, chemical structures of putative non-peptide inhibitors of the altered conformation are revealed.

A second embodiment of the invention is a method of generating, in silico, chemical structures of putative non-peptide inhibitors of a biologically-active receptor. Here, the method comprises first obtaining empirical three-dimensional data of the receptor bonded to a proteinaceous or non-proteinaceous ligand, the receptor and the ligand bonded thereto collectively referred to as a receptor-ligand complex. Then a model of the receptor-ligand complex is constructed in silico using the three-dimensional data. Then, the ligand is excised from the model of the receptor-ligand complex, thus yielding an in silico model of a conformation of a binding site on the receptor. Then, the model of the conformation of the binding site is altered (in chemically plausible ways) to yield a model of an altered conformation of the binding site. In silico models of non-peptide chemical structures are then generated that are complementary in structure to the altered conformation of the binding site. Structures of putative non-peptide inhibitors of the altered conformation are thus revealed.

A third embodiment of the invention is a method of generating chemical structures of putative non-peptide inhibitors of a biologically-active receptor. In this embodiment, the method comprises obtaining three-dimensional data of the receptor bonded to a proteinaceous or non-proteinaceous ligand, the receptor and the ligand bonded thereto collectively referred to as a receptor-ligand complex. Then constructing a model of the receptor-ligand complex in silico using the three-dimensional data, thereby yielding an in silico model of a conformation of a binding site on the receptor when the binding site is occupied by the ligand. Departing from the first two embodiments, in the third embodiment, the model of the conformation of the binding site is minimized to identify residues within the binding site that are mobile and proximal to the ligand. In silico models of non-peptide chemical structures that are complementary in structure to the minimized conformation model are then generated. Thus structures of putative non-peptide inhibitors of the minimized conformation model are revealed.

DETAILED DESCRIPTION OF THE INVENTION

For sake of brevity and clarity, the discussion that follows is limited largely to an investigation into the rational design of inhibitors of aspartic peptidases using the method according to the present invention. The same methodology as described herein can be used to investigate any receptor-ligand or enzyme-substrate complex, without limitation. Aspartic peptidases were chosen as an illustrative enzyme for investigation because of their clinical importance in a number of disease states and the large amount of prior art information regarding this ubiquitous class of enzymes.

Three-Dimensional Data:

In order for the present invention to be practiced, there must be three-dimensional data on the structure of the receptor-ligand complex to be investigated. Preferably, this data takes the form of X-ray crystallographic data or X-ray crystallographic data in combination with high resolution NMR data on the receptor-ligand complex. Obviously, the higher the resolution of the data, the more finely detailed will be the results. Note, however, that the manner in which the three-dimensional data is generated is irrelevant to the practice of the invention. Thus, the data can be acquired by any means now known in the art or developed in the future.

X-ray crystallography is very well known in the art and has been the primary means of determining protein structure since the formulation of Bragg's Law in 1913. It will not be described in any great detail herein because a person of ordinary skill in the art can access the required information and equipment needed to gather and analyze X-ray crystallographic data. In short, X-ray crystallography is an experimental technique that exploits the fact that X-rays are diffracted by crystals. X-ray crystallography is not, however, an imaging technique. It is a technique that maps electron density. X-rays have a wavelength in the Ångström range ($\sim 10^{-8}$ cm) and thus are scattered by the electron cloud of an atom of comparable size. Based on the diffraction pattern obtained from X-ray scattering off the periodic repeating unit cell of a crystal, the three-dimensional electron density of the unit cell can be reconstructed. Additional phase information must also be extracted to complete the density map, either from the diffraction data itself or from additional diffraction experiments where the crystal has been doped with a heavy metal atom at known locations. A model is then progressively built based the experimental electron density and refined against the data generated from different crystals. The result is a very accurate, three-dimensional structure of the crystallized molecule.

A tremendous amount of three-dimensional data is in the public domain and available on-line through the Research Collaboratory for Structural Bioinformatics, as well as other sources. This non-profit organization maintains the Protein Data Bank, a repository for structural information on proteins. The Protein Data Bank can be accessed and searched by key word on the Internet at rcsb.org/pdb.

Thus, if the receptor/ligand complex to be studied has already been crystalized and the raw X-ray crystallographic data acquired, the structural data required to begin the subject method can very likely be obtained through the Protein Data Bank. Otherwise, the investigator must first generate the required three-dimensional data.

Other publicly-accessible sources for X-ray crystallographic data include the SouthEast Collaboratory for Structural Genomics (secsg.org/secsg/default.html) and the Georgia X-Ray Crystallography Center of the University of Georgia (Athens, Ga.).

Molecular Modeling Computer Programs:

The method described herein utilizes the computational power of modern computers to model receptor binding sites and to provide information, based upon physical and chemical considerations, on the suitability of a given molecule to fit within a given receptor binding site. A host of such programs are available commercially and are suitable for use in the present invention.

The preferred program, and the program used in the Examples below, is a program called "GrowMol." The program itself is described in great detail in the prior art: see Bohacek & McMartin (1992) *J. Med. Chem.* 35(10): 1671–1684; Bohacek & McMartin (1994) *J. Am. Chem. Soc.* 116:5560–5571; Bohacek & McMartin (1995) *SIAM J. Math Anal.* 116:147–179; Bohacek, McMartin, & Guida (1996) *Med Res. Rev.* 16(1):3–50; Rich, Bohacek, Dales, Glunz & Ripka (1996) in *Actualites de chimie therapeutic*, Elsevier: Amsterdam 101–111; and Ripka & Rich (1998) *Curr. Op. in Chem. Biol.* 2:441–452.

The program can be obtained from a number of university sources, including from Daniel H. Rich at the University of Wisconsin-Madison. The program can also be obtained directly from its principal author, Regine Bohacek of Boston De Novo Design, Boston, Mass.

The "GrowMol" program is capable of generating organic structures that are both spatially and chemically complementary to a mathematically-defined receptor binding site. The program mathematically constructs molecules, one atom at a time, to occupy the mathematically-defined space of a binding site. In this fashion, the "GrowMol" program can be used to generate chemical structures whose physical and chemical properties are complementary to the receptor binding site. At each reiteration of the construction process, the position and type of atom to be added to the model are randomly selected using Boltzmann statistics, in an effort to bias acceptance toward atoms that can form favorable interactions with the binding site.

Another computer program that is very useful in conjunction with the "GrowMol" program is called "Flo." The "Flo" program is a molecular modeling program written by Colin McMartin. The program aids in visualizing molecules and in designing lead drug compounds. The "Flo" program is available online at uwmml.pharmacy.wisc.edu/Flo/floindx.html. The "Flo" program is also marketed commercially through Thistlesoft Software Co., Morris Town, N.J. The "Flo" program can also be obtained directly from its author, Colin McMartin, at cmcma@ix.netcom.com. The great advantage of using the "Flo" program in conjunction with the "GrowMol" program is that the "Flo" program provides a front-end graphical interface that enables molecular models to be formatted more easily for analysis using the "GrowMol" program.

While the "GrowMol" program is the preferred program of the present inventors, a very large number of equally suitable chemical modeling programs are available commercially or through academic outlets. For example, Tripos of St. Louis, Mo., markets a very wide range of molecular modeling and analysis programs, including the "Advanced Computation," "AMPAC," "CONFORT," "MM3(2000)," "MOLCAD," and "SYBYL/Base" programs.

Briefly, the "Advanced Computation" program provides a wide range of tools for conformational analysis, including calculations that enumerate all possible torsional states of a molecule or identify just its low-energy conformations.

The "AMPAC" program calculates structures and electronic properties of molecules using semi-empirical quantum mechanical methods.

The "CONFORT" program performs conformational analyses of drug-sized molecules to identify the global minimum energy conformer, all local minima within a user-specified energy range, or a maximally diverse subset of conformers.

The "MM3(2000)" program is a molecular mechanics program that produces high-quality three-dimensional structures and computes molecular energy, vibrational spectra, and a variety of thermodynamic and spectroscopic quantities.

The "MOLCAD" program creates and displays molecule surfaces onto which it maps key properties, including lipophilicity, electrostatic potential, hydrogen bonding sites, and local curvature.

The SYBYL/Base program includes a comprehensive suite of sub-programs for molecular modeling, including structure building, optimization, and comparison; visualization of structures and associated data; annotation, hardcopy and screen capture capabilities; and a wide range of force fields.

Accelrys Inc. (San Diego, Calif.), a subsidiary of Pharmacopeia Inc., is another commercial supplier of suitable molecular modeling software for use in the present invention. Accelrys Inc. was formed in June of 2001 through a five-way merger of the molecular modeling companies Molecular Simulations Inc., Synopsys Scientific Systems, Oxford Molecular, GCG, and Synomics Ltd. As noted above, the present invention requires three-dimensional data on the target receptor-ligand complex. Accelrys' "QUANTA" program can be used for processing of X-ray data, electron density fitting, and model building; the "CNX" program can be used for phasing and refining of the initial X-ray model. If NMR data is available for the receptor-ligand complex, Accelrys' "FELIX" and "Insight II" NMR modules can be used for spectral data processing, and for refining and evaluating putative structures and conformations.

Accelrys also markets a line of "Insight II" modules, including the "MODELER," "Biopolymer," "Homology," "SeqFold," and "Binding Site Analysis" modules. These programs can be used to model and to predict protein structure.

As noted above, macromolecules are not static structures. They move, vibrate, and interact with other molecules and their environment. Understanding these movements and interactions is essential for constructing an accurate model of the receptor-ligand complex. Accelrys markets a program, "CHARMm," for dynamic modeling of macromolecules. The "Insight II" program also includes modules capable of dynamic molecular modeling, including the "Discover," and "Decipher" modules. The "QUANTA" program is also capable of dynamic modeling. Yet another Accerlrys program, "Cerius2" enables dynamic modeling, especially when using the "Cerious2" modules "C2.OFF" and "C2.CFF."

Taken together, these programs from Accelrys enable model building of small molecules and biomolecules, graphical model manipulation, energy minimization, graphical trajectory display, and data analysis.

A number of other companies, as well as academicians, have also released molecular modeling programs that can be used in the present invention. A great many of these programs can be obtained through IBM's High Performance Computing Division, Armonk, N.Y. A non-exhaustive list of suitable programs available through IBM and the names of the original suppliers includes the following:

| Supplier Name | Program(s) |
| --- | --- |
| CCP4 Consortium | CCP4 |
| | SQ |
| University of Vienna | VASP/VAMP |
| Univ of Cal. at San Francisco | AMBER 6 |
| SemiChem | AMPAC |
| CAChe (Fujitsu) | CONFLEX Extended |
| | Huckel |
| | Molecular Dynamics |
| | Tabulator |
| | ZINDO |
| | MOPAC |
| | Molecular Mechanics |
| Iowa State University | GAMESS |
| Gaussian Inc. | Gaussian 98 |
| Schrodinger | Jaguar |
| | MOPAC2000 |
| | Macromodel |
| University of Birmingham | MOLPRO ** |
| Pacific Northwest National Lab | NWChem |
| Accelrys (see above) | OFF Dynamics |
| | OFF Minimize |
| | Discover |
| | DMOL |
| | CHARMm |
| | DGAUSS |
| | Polymorph |
| | Predictor |
| Qchem | QChem |
| University of Minnesota | AMSOL 6.6 |
| University of Ottawa | DEFT |
| Thistlesoft | FLO/QXP |

Another program that can be utilized in the present invention is called DEZYMER, developed by Homme Hellinga of Duke University. See Hellinga & Richards (1991) *J. Mol. Biol.* 222:763–785; and Hellinga, Caradonna, & Richards (1991) *J. Mol. Biol.* 222:787–803.

The plausible conformations of the receptor binding site, as well as the ability for a given non-peptide peptidomimetic to fit within a given conformation can also be modeled in silico using Monte Carlo methods. Numerical methods known as Monte Carlo methods can be loosely described as statistical simulation methods, where statistical simulation is defined in general terms to be any method that utilizes sequences of random numbers to perform the simulation. Monte Carlo methods have been used for centuries, but only in the past several decades has the technique gained the status of a full-fledged numerical method capable of addressing the most complex applications. The name "Monte Carlo" was coined during the Manhattan Project of World War II, due to the similarity of statistical simulation to games of chance, and because the capital of Monaco (i.e., Monte Carlo) is a center for gambling and similar pursuits.

Monte Carlo is now used routinely in many diverse fields, from the simulation of complex biological phenomena and the simulation of sub-nuclear processes in high-energy physics experiments, to the mundane, such as the simulation of a Bingo game. The analogy of Monte Carlo methods to games of chance is quite apt, but the "game" to be analyzed here is the plausible conformations of the binding site of a receptor, and the outcome of the game is not a pot of money, but rather a solution to the problem of determining the shape of a non-protein peptidomimetic that will bind to one or more of the plausible conformations of the binding site.

Statistical simulation methods such as Monte Carlo can be contrasted to conventional numerical discretization methods, which typically are applied to ordinary or partial differential equations that describe some underlying physical or mathematical system. In most applications of Monte Carlo, the physical process is simulated directly, and there is no need even to write down the differential equations that describe the behavior of the system. The only requirement is that the physical system, in this case, the receptor-ligand complex, be described by probability density functions (pdf's). Insofar as X-ray crystallographic data yields an electron density map, these data are very well suited for analysis via Monte Carlo methods. Once the pdf's are known, the Monte Carlo simulation can proceed by random sampling from the pdf's. Many simulations are then performed reiteratively (multiple "trials" or "histories") and the desired result is taken as an average over the number of observations (which may be a single observation or perhaps millions or billions of observations).

Regardless of the system being modeled, every Monte Carlo approach shares certain major components. A full discussion of these components, as well as the physical and mathematical underpinnings of the same, is available in the prior art and accessible to one of ordinary skill in the art. Thus, a complete discussion of Monte Carlo methods will not be included herein. A good starting point is "Introduction to Monte Carlo Methods"© 1996, Computational Science Foundation Project, Verena Meiser, Ed. (Vanderbilt University, Nashville, Tenn.) (sponsored by the U.S. Department of Energy).

The primary components of a Monte Carlo simulation method include the following:

A set of probability distribution functions (pdf's): the physical system, i.e., the geometry and chemistry of the receptor-ligand complex, is described by a set of pdf's.

A random number generator: a source of random numbers uniformly distributed on the unit interval must be available.

A sampling rule: a prescription for sampling from the specified pdf's, assuming the availability of random numbers on the unit interval, must be given.

Scoring (or tallying): the outcomes must be accumulated into overall tallies or scores for the quantities of interest (bond lengths, angles, rotation, steric interactions, etc.).

Error estimation: an estimate of the statistical error (variance) as a function of the number of trials and other quantities must be determined.

Variance reduction techniques: methods for reducing the variance in the estimated solution to reduce the computational time for Monte Carlo simulation.

Parallelization and vectorization: algorithms to allow Monte Carlo methods to be implemented efficiently on advanced computer architectures.

Using these foundational elements, the plausible conformations of a receptor-binding site can be modeled and analyzed via a Monte Carlo approach that is implemented on a programmable computer.

Rational Design of Non-Peptide Peptidomimetics:

The long-sought and unrealized goal of peptidomimetic research is to devise methods to generate non-peptide inhibitors based upon the three-dimensional data of protein receptors and protein receptor/protein ligand complexes. In short, there is a long-felt need for a method to generate non-peptide inhibitors on a rational basis, starting from the empirically-derived three-dimensional coordinates of receptor-ligand complexes. A universal method for converting peptide-based inhibitors into non-peptide inhibitors would revolutionize the drug discovery process because a major stumbling block in drug design is obtaining compounds with appropriate bioavailability.

For several years, attempts have been made by the present inventors to utilize structure-generating programs to design novel non-peptide peptidomimetics. As described in the Examples, however, by modeling the binding site of an enzyme-substrate complex, and then mathematically altering the geometry of the binding site, the present method was used to "re-discover" known tight-binding peptide-derived inhibitors related to pepstatin.

The known inhibitors discussed herein and in the Examples (piperidine compounds 1–5) presented a unique challenge because the binding modes of these piperidines are fundamentally different than the peptide-derived peptidomimetics.

As described herein, the present inventors have shown it possible to find the piperidine class of inhibitors, a priori, by use of computer modeling of altered binding site conformations, using peptide-derived peptidomimetic crystallographic data as an empirical starting point. Successful demonstration of this strategy is extremely important and novel. In short, it provides a means to develop fundamentally novel inhibitors based on empirical data obtained from a peptide-derived inhibitor.

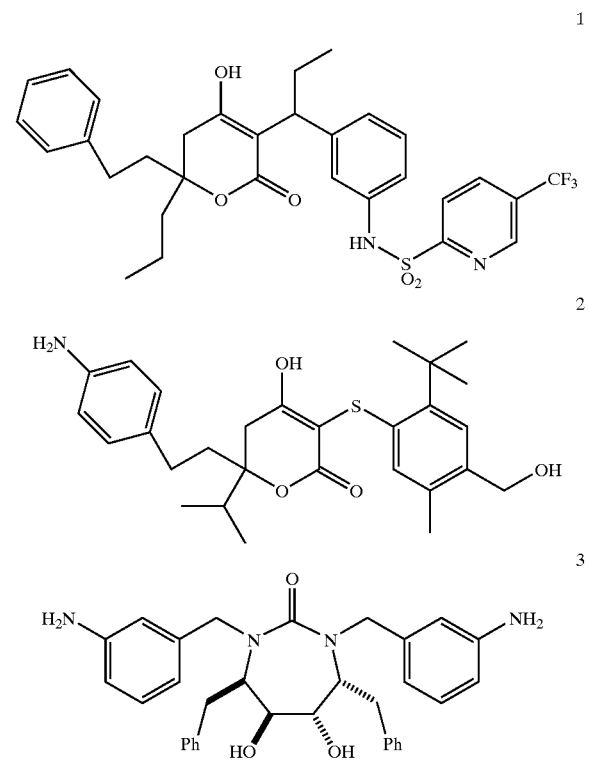

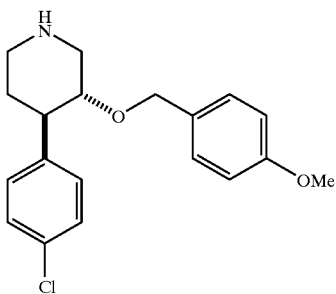

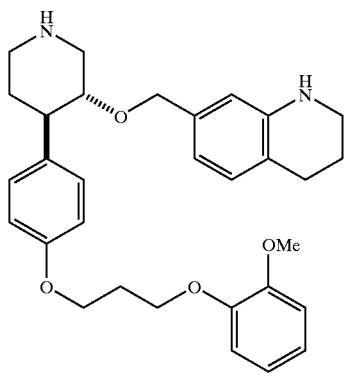

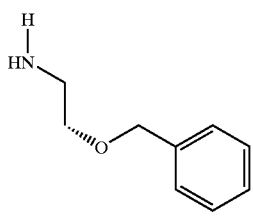

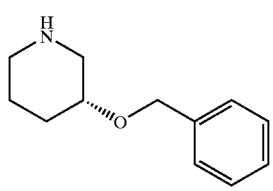

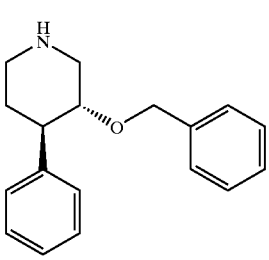

4

5

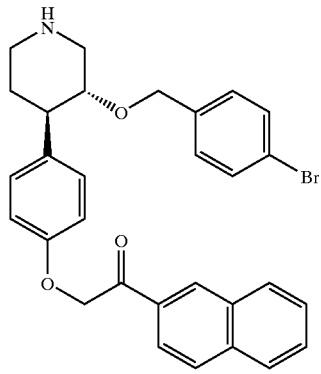

5

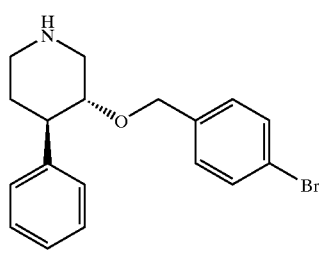

8

9

10

In the Examples two aspartic peptidases for which no piperidine inhibitors had been reported were investigated to determine if the same method would work for other aspartic peptidases. As described in the Examples, beginning with the X-ray structure of a known statine-based peptide inhibitor bound to porcine pepsin, an attempt was made to "grow" the piperidine unit of compounds 1–5 from the $P_1$ S-benzyl side-chain. However, growth from this point on CySta towards the catalytic carboxyl groups of the pepsin only generated straight chain amines. The "flap" within the model of the binding site was then mathematically raised about 1 Å. This alteration to the model generated a series of piperidines (compound 9) which lacked the C4 substituent of compound 4 or 5. (See the Example.) Molecular modeling revealed that a −120° rotation of $C^1$ in Tyr75 provided the space needed for the piperidine C4-phenyl group. After implementing these active site conformational changes in the model, running the "GrowMol" program resulted in the 3,4-disubstituted piperidine compound 12, a direct analog of the known inhibitor compound 4.

Further rotation within the model of Trp39, followed by structure generation using the "GrowMol" program, gave the acetonaphthone analog 11. This structure is closely related to the known inhibitor compound 5. After synthesis and testing, piperidines 11 and 12 inhibited R. chinensis and porcine pepsin with $IC_{50}$ values of 0.2 and 2.0 μM respectively.

The "re-discovery" of the 3,4-disubstituted piperidines as renin inhibitors and the extension of the strategy used to find them to other aspartic peptidases demonstrates that the structural information provided from the peptide-based inhibitors can be used to design non-peptide peptidomimetics. It is critical to note that successful generation of these non-peptide peptidomimetics required exploration of an enzyme active site topography not apparent in the crystal structures of either the native enzyme or the enzyme/peptide-derived inhibitor complexes. This new active site conformer was found by altering the model of the active site in mechanistically-rational ways and then modeling complementary inhibitor molecules to fit the altered active site.

The discovery of the compounds 8–12 using the present method (see the Examples), their correlation to known non-peptide inhibitors, and their correlation with peptide-derived inhibitors represents a peptidomimetic "Rosetta Stone" of sorts. Understanding how two distinctly different inhibitor structures can fit into two enzyme active site topographies that differ in substantial, but mechanistically-related ways, made it possible to extend the process to two other aspartic peptidases, pepsin and *R. chinensis* pepsin. It must be emphasized that these peptidomimetics stabilize an enzyme conformation that is different from the extended β-strand binding conformation that binds all previously known peptide-derived and non-peptide inhibitors. Thus, the present invention is a method of rationally designing inhibitors by analyzing novel enzyme conformations outside the normally observed conformations.

As receptor conformational mobility is likely to occur in the vast majority, if not all, biological targets, the method described herein is quite general. At any interface between an enzyme and its substrate or at a protein-protein interface (i.e., the interface between a receptor and ligand), it is possible, using the present invention, to determine if residues or residue side chains within the enzyme or receptor can move into new positions, thereby generating structural voids into which potential inhibitors can fit. Inhibitors thus can be designed and synthesized to complement each novel conformation of the binding site. In this fashion, the starting point for inhibitor design is rational, as opposed to the random or semi-random approach inherent in high-throughput screening.

In the Examples, the optimized renin inhibitors bind to an enzyme active site conformation formed by synchronous movements of three side chains: The C4-phenyl group binds to the enzyme to replace Tyr75, which was rotated to another position in the computer model. Interestingly, Leu73 rotates to fill some of the Tyr75 pocket, and this in turn allows Trp39 to occupy a new site formed in part by the vacated Leu73. This cascade of conformational transitions in the renin model allows the optimized inhibitor to stabilize an enzyme conformation with multiple alterations not observed with binding of the classic substrate-derived peptidomimetics.

Aspartic Proteases:

The aspartic peptidases are an extensively characterized class of enzymes with a large number of native and enzyme-inhibitor crystal structures presently available. The aspartic peptidases generally comprise two structural domains (the N- and C-termini) that define the active site, along with a hairpin turn structure, or "flap" region that covers the enzyme active site (HIV protease contains 2 flaps). Structural considerations strongly indicate that during catalysis the flap must be open to allow the substrate to enter into the active site. The flap must close to promote catalysis. Finally, the flap must re-open to allow diffusion of the products from the active site.

The aspartic peptidases catalyze the cleavage of a peptide amide bond via a general acid-base mechanism. These peptidases have two Asp-Thr-Gly sequences lining the active site and contain a water molecule bound between the two catalytically active Asp residues. This substrate water molecule is activated by the aspartic acids for nucleophilic attack on the substrate amide carbonyl to generate a tetrahedral intermediate, which is observed as a low energy species in molecular dynamic-ab initio calculations. Piana, Carloni, & Parrinello (2001) Role of Conformational Fluctuations in the Enzymatic Reaction of HIV-1 Protease, manuscript submitted. The amide nitrogen is eventually protonated leading to the collapse of the tetrahedral intermediate and subsequent release of the amide bond hydrolysis products from the active site.

Aspartic peptidase inhibitors have been designed to treat hypertension, malaria, AIDS, and Alzheimer's disease, and this list is expected to increase as genomic sequencing continues. Over the years, a number of native and enzyme-inhibitor crystal structures have been solved for both the medicinally relevant aspartic peptidases (renin, plasmepsin, HIV protease, β-secretase, and cathepsin D) and model peptidases (penicillopepsin, endothiapepsin, chymosin, pepsin, and *Rhizopus chinensis* pepsin). Both peptide-derived and non-peptide inhibitors have been developed and the relationships between the different peptidomimetics can be analyzed in terms of enzyme-inhibitor crystal structure complexes.

A key structural element in most inhibitors of aspartic peptidases is a hydroxyl or hydroxyl-like moiety that binds to the two catalytically active aspartic acids in place of the Asp-bound water molecule. For example, the unnatural amino acid statine, found in the peptide natural product pepstatin, was postulated to mimic the amide bond hydrolysis transition-state. A number of other mechanism pathway inhibitors have been invented and subsequently developed into useful aspartic peptidase inhibitors:

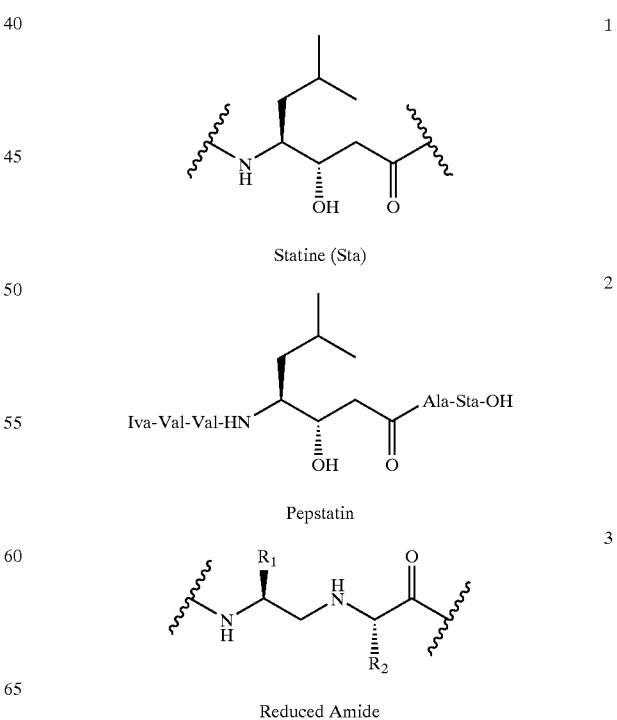

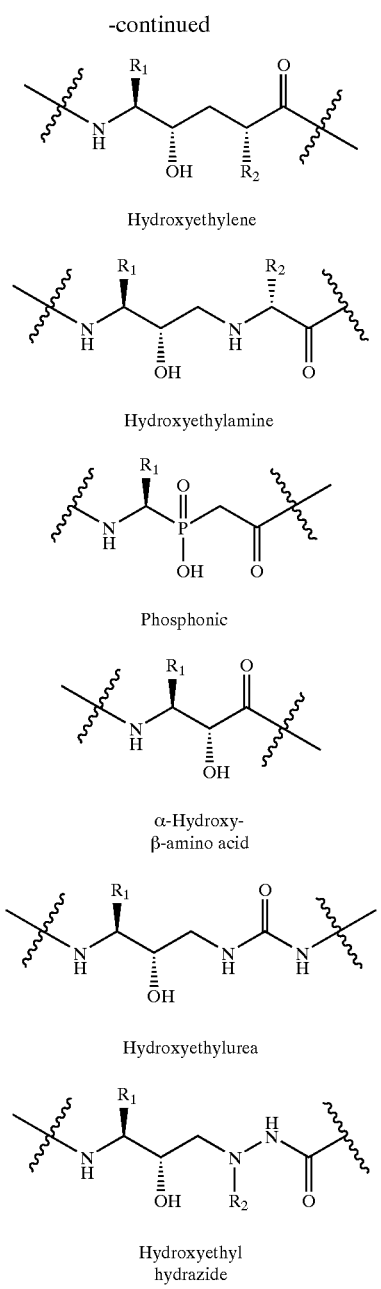

Hydroxyethylene

Hydroxyethylamine

Phosphonic

α-Hydroxy-
β-amino acid

Hydroxyethylurea

Hydroxyethyl
hydrazide

Notable are the hydroxyethylene and the hydroxyethylamine, the latter of which was employed extensively in the development of HIV protease inhibitors. Lebon & Ledecq (2000) *Curr. Med. Chem.* 7:455–477.

These inhibitors were originally designed to be transition state analogs (TSA) for the enzyme-catalyzed amide bond hydrolysis. However, recent calculations by Carloni have shown the critical inhibitor hydroxyl group binds to the HIV protease bis-protonated form of the catalytic dyad, not to the mono-protonated form implicated in the catalytic mechanism. Piana et al. (2001) *J. Am. Chem. Soc.* 123:8730–8737. It has been suggested that these inhibitors bind to the isomechanism form of the enzyme discovered by Northrop. Northrop (2001) *Acc. Chem. Res.* 34:790–797. Consequently pepstatin, and by analogy other effective peptide-derived inhibitors of aspartic peptidases, contain elements of collected-substrate inhibition as proposed earlier. These findings are consistent with the fact that the best inhibitors of aspartic proteases are one-atom extensions of an isosteric replacement of the substrate backbone, i.e., hydroxyethylamines and related analogs.

Selective aspartic peptidase inhibitors have been designed by replacing the specific peptidase substrate dipeptidyl cleavage site with a TSA dipeptide mimic (see the structures immediately above). The principles of this strategy were first utilized to develop selective inhibitors for the model aspartic peptidases and have been extended (Table 1) to renin, HIV protease and β-secretase, all of which are therapeutically promising aspartic peptidases. Replacement of the dipeptidyl cleavage site of a native substrate with a TSA effectively generates an inhibitor that: 1) is specific for the peptidase; 2) recognizes the transition state analog side chains; and 3) recognizes amino acid side chains both upstream and downstream from the cleavage site. The enzyme active site is buried in a deep cleft capable of accommodating up to nine amino acid residues of the substrate/inhibitor with the inhibitor's exquisite selectivity obtained by the complementary interaction between the enzyme binding sites ($S_6$–$S_3'$) with the inhibitor (the $P_6$–$P_3'$) residues. Some renin inhibitors have also been shown to bind to a new sub-pocket ($S_3^{sp}$), which provides a method to increase both inhibitor potency and selectivity. (Rahuel, J., et al. (2000) *Chem. Biol.* 7:493–504.)

TABLE 1

Examples of Selective Transition State
Analog Inhibitors of Aspartic Peptidases

Enzyme Target    Selective Inhibitor

Renin

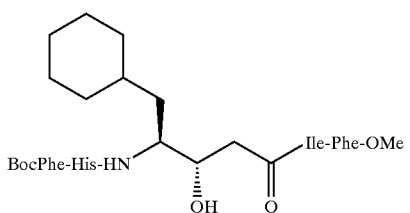

BocPhe-His-HN — ... — Ile-Phe-OMe

TABLE 1-continued

Examples of Selective Transition State
Analog Inhibitors of Aspartic Peptidases

Enzyme Target  Selective Inhibitor

Renin 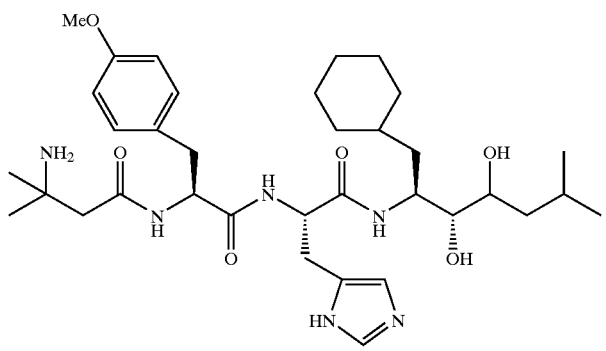

Renin 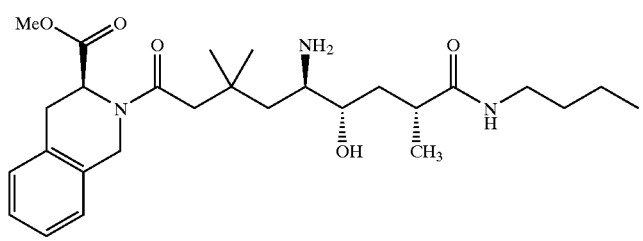

HIV Protease
JG-365
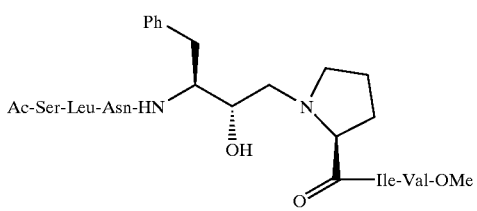

HIV Protease
U-85548e
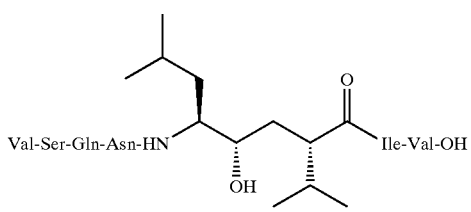

β-secretase 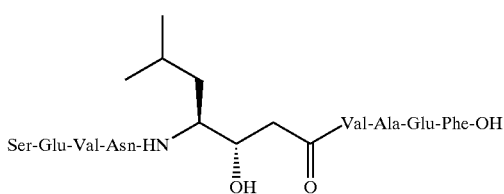

β-secretase 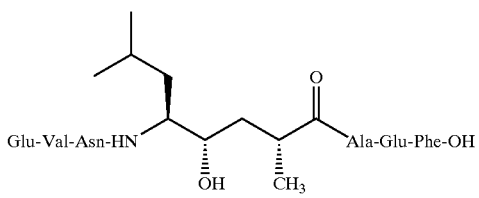

Unfortunately, very few of the first generation of peptide-based aspartic peptidase inhibitors proved clinically useful due to limited oral bioavailability. As a result the first pharmaceutical attempts to convert an aspartic peptidase (renin) inhibitor into a clinically useful treatment for hypertension via TSA-based inhibitors proved to be a monumental failure.(41) Lien, Gao, & Lien (1994) *Progress in Drug Research* 43:43–86. It was eventually realized, after extensive modifications to the ancillary peptide functionality, that developing bioavailable peptide-derived inhibitors critically depended on the molecular weight of the inhibitor. In contrast, developing inhibitors for HIV protease was substantially easier than for renin because HIV protease recognizes a significantly smaller minimum substrate sequence. Some of the highly modified HIV protease inhibitors now in clinical use have excellent oral bioavailability and establish that application of this design process can be very successful in favorable cases:

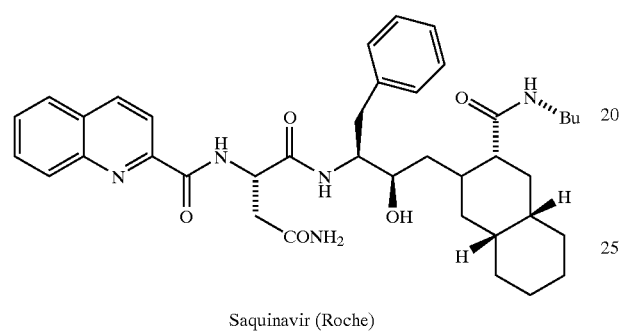

Saquinavir (Roche)

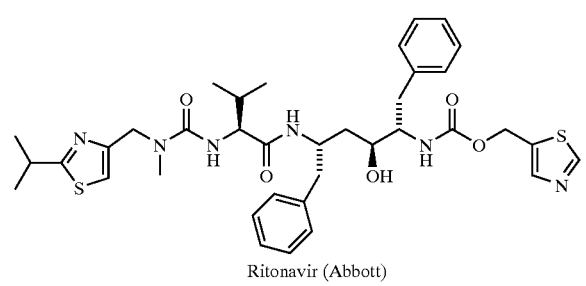

Ritonavir (Abbott)

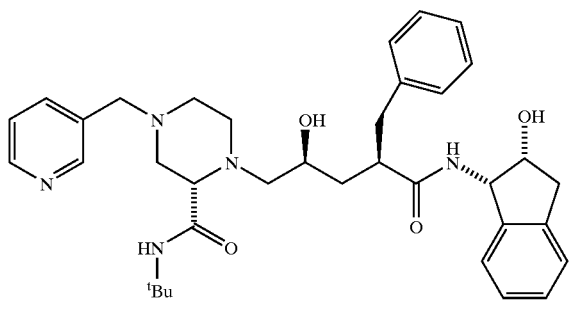

Indinavir (Merck)

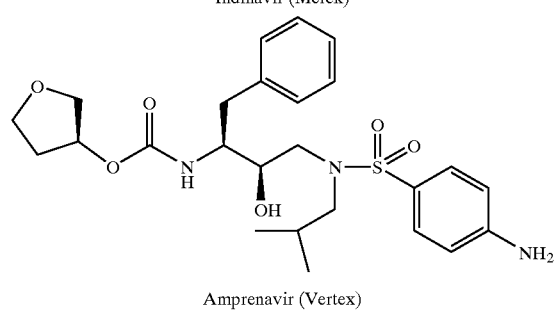

Amprenavir (Vertex)

-continued

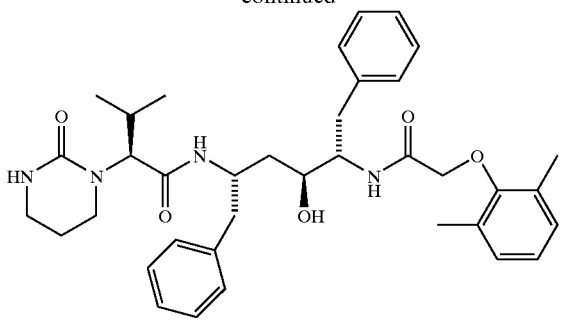

Lopinavir (Abbott)

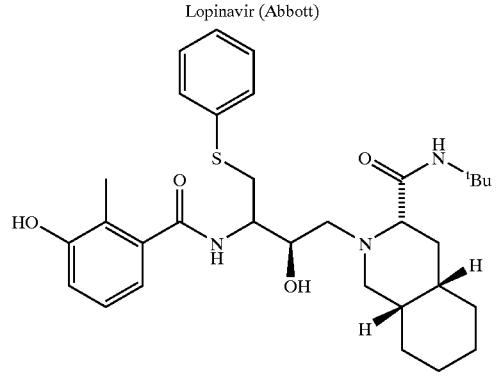

Nelfinavir (Agouron)

Peptide-Derived Transition State Analog Inhibitors of HIV Protease Used in AIDS Therapies Recent literature describing the development of peptidomimetic inhibitors rarely defines the term "peptidomimetic." Thus, the term is often applied to a variety of different structural types.[42] For example, peptide analogs that contain one or more amide bond replacements have sometimes been called peptidomimetics. See Spatola, "Peptide backbone modifications: a structure-activity analysis of peptides containing amide bond surrogates, conformational constraints, and related backbone replacements" in *Chem. Biochem. Amino Acids, Pept., Proteins*; Weinstein, B., Ed.; Marcel Dekker, Inc: New York, 1983; pp 267–257. Peptide analogs that contain a conformationally restricted amino acid unit or other conformational constraint have been called peptidomimetics. See Hart & Rich, "Stereochemical aspects of drug action I: Conformational restriction, steric hindrance and hydrophobic collapse," in *Pract. Med. Chem.*; Wermuth, C., Ed.; Acad. Press: London, UK, 1996; pp 393–412. These types of peptidomimetics are essentially amino acid mimetics pieced together in a linear fashion to mimic the normal biologically-active peptide substrate. In contrast, Farmer initially proposed the term peptidomimetic to describe potentially novel scaffolds designed to replace the entire peptide backbone while retaining isosteric topography of the enzyme-bound peptide (or assumed receptor-bound) conformation. Farmer, "Bridging the gap between bioactive peptides and nonpeptides: some perspectives in design," in *Drug Design*; Ariens, E. J., Ed.;

Academic Press: New York; Vol. 10, pp 119–143. Heterocyclic natural products or screening leads that bind to peptide receptors also have been called peptidomimetics by virtue of their mimicking (or antagonizing) the function of the natural peptide. For a compilation of the terminology see Fletcher & Campbell (1998) *Chem. Rev.* 98:763–795. Although confirmation of mimicry via structural data is rarely available for receptor-bound ligands (Ripka & Rich (1998) *Curr. Opin. Chem. Biol.* 2:441–452), ample evidence establishes that some heterocyclic inhibitors do mimic the extended β-strand of enzyme-bound substrate-derived inhibitors. In these cases, the term peptidomimetic as defined by Farmer, supra, is appropriate even though the inhibitor lead structure was not designed. For a discussion of the preference for designed peptidomimetics see Olson et al. (1993) *J. Med. Chem.* 36:3039–3049.

For peptidomimetic peptidase inhibitors, a definition based on the topography of the inhibited enzyme active site and the chemical composition of the inhibitor has been suggested. Bursavich, West, & Rich (2001) *Org. Lett.* 3:2317–2320. Many peptidase inhibitors, e.g. 110 and 111, are actually amino acid and transition-state mimics pieced together to emulate the ligand-bound extended β-strand substrate conformation of other peptide-derived inhibitors and consequently they retain considerable peptide character. For example, the co-crystal structure of 111 bound to HIV protease demonstrated that the enzyme-bound inhibitor successfully mimicked the extended β-strand binding conformations found for a variety of other HIV protease inhibitors. Martin et al. (1999) *Biochemistry* 38:7978–7988. These types of are defined herein as "peptide-derived peptidomimetics" to highlight their close structural relationship with the enzyme-bound peptide-substrate conformation. Notably the elegant pyrrolinone mimics of enzyme-bound extended β-structures (e.g., compound 110) illustrate a sophisticated version of this type of peptidomimetic. This compound stabilizes both intra- and intermolecular hydrogen bonds. The ability of the compound to bind to both of these two conformers is thought to provide improved bioavailability.[51]

All other inhibitors are designated herein as non-peptide peptiodomimetics. For example, structurally distinct heterocyclic aspartic peptidase inhibitors, e.g. 112 and 113, have been discovered either via high-throughput screening (HTS) or rational design methods. These inhibitors are designated herein as non-peptide peptidomimetics because of their remote structural relationship to native peptide substrates.

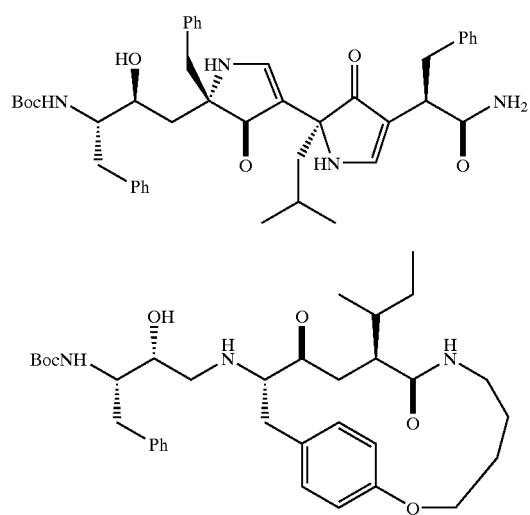

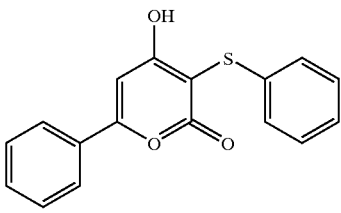

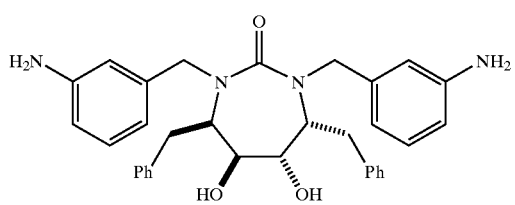

Examples of Known Peptidomimetics (110 & 111: Peptide-Derived; 112 & 113: Non-Peptide)

Most importantly, comparison of these two peptidomimetic classes reveals that the active site topography accessed by the non-peptide peptidomimetics is nearly identical to that accessed by the peptide-derived peptidomimetics. In effect, these structurally distinct compounds selectively stabilize the same enzyme conformation within the complete ensemble of enzyme conformations. This is not completely surprising because the structural evolution of the non-peptide inhibitors was guided by consideration of the bound-conformations of known peptide-derived inhibitors.

Ideally, a major goal of the medicinal chemist is to discover novel structures with pharmacodynamic properties that enable both oral and CNS bioavailability and suitable duration of action. This necessitates developing new compounds that circumvent the multiple export and metabolism mechanisms that exist to control levels of active peptides in vivo. The present invention, however, yields structures that are rationally designed to target the ensemble of conformations not accessed by previously designed inhibitors. In short, by modeling and rationally altering receptor binding site conformations, new information is revealed that can then be used to design inhibitors specific to the altered and novel conformation.

The first indication that aspartic peptidase active sites are conformationally flexible arose from studies of the model enzyme penicillopepsin in the late 1970s. James and co-workers solved the structure of a known irreversible inhibitor of the aspartic peptidases, 1,2-epoxy-3-(p-nitrophenoxy)propane (EPNP), covalently attached to penicillopepsin in 1977. James, Hsu, & Delabaere (1977) *Nature* 267:808–813. This structure demonstrated that a molecule of EPNP was covalently bound to both catalytically active aspartic acid residues (Asp32 and Asp215) and that the bound water molecule was displaced from the enzyme active site. Also, a major conformational change was observed for the Tyr75 side chain. The rotation of the Tyr75 phenolic ring led James to hypothesize participation of Tyr75 as a proton donor in the enzyme-catalyzed amide bond hydrolysis, in analogy to the role of Tyr48 in carboxypeptidase A. However, when later enzyme-inhibitor crystal structures demonstrated the location of Tyr75 in its unrotated native position, James withdrew his proposal (James et al. (1982) *Proc. Natl. Acad. Sci. U.S.A.* 79:6137–6141) and the rotation of Tyr75 in penicillopepsin has not been further examined since. Yet this was the first detailed demonstration of conformational flexibility in the aspartic peptidases. The potential of Tyr75 to rotate into alternate locations has important implications for the development of novel inhibitors. The significance of this mobility has never been recognized until now.

In 1982, an important conformational transition was discovered from the X-ray structure of a statine-based peptide inhibitor bound to penicillopepsin. Although a variety of pepstatin-based peptide inhibitors had been synthesized, only one peptide, Iva-Val-Val-StaOEt, co-crystallized with penicillopepsin in a form suitable for X-ray structural determination. James and co-workers solved the structure of the complex (James et al. (1982), supra). It showed that the critical 3S-hydroxyl group was hydrogen bonded to the catalytic aspartic acid groups and displaced an enzyme-bound water molecule. This binding mode was similar to the pepstatin-pepsin co-crystal structure, but an important structural change was observed for the first time. In the native penicillopepsin structure, the "flap region" (comprising residues Trp71-Gly83) was found in an "open" conformation that did not obstruct the enzyme active site cleft. James & Sielecki (1983) *J. Mol. Biol.* 163:299–361. However, the crystal structure of the enzyme-inhibitor complex showed significant conformational changes in the flap that enabled this segment to close upon the inhibitor bound within the active site. The binding resulted in a movement of the tip of the β-hairpin turn structure by approximately 4 Å toward the catalytic groups, thereby trapping the inhibitor.

Crystal structures of chymosin, a bovine aspartic peptidase closely related to other mammalian aspartic peptidases, revealed additional unexpected conformational changes. In the native enzyme, the flap was rotated into an "open" conformation similar to native penicillopepsin. Newman et al.(1991) *J. Mol. Biol.* 221:1295–1309; Gilliland et al. (1990) *Proteins: Struct., Funct., Genet.* 8:82–101. But more surprising was the observed 180° rotation of Tyr75 into the region normally occupied by an inhibitor/substrate $P_1$ substituent. For several years, attempts to obtain chymosin-inhibitor complexes had failed; only native enzyme crystals were obtained. This could be attributed to the rotation of Tyr75 into a position that blocked substrate-like molecules from binding.

Eventually, Groves and coworkers obtained crystals of the known renin inhibitor CP-113971 bound to chymosin and solved the crystal structure Groves et al. (1998) *Protein Eng.* 11:833–840. This structure revealed a remarkable conformational mobility of Tyr75. Comparison of native and enzyme-inhibitor crystal structures revealed the aspartic peptidase flap had "closed" over the inhibitor in the active site by moving approximately 4 Å toward the catalytically active groups compared with the native enzyme structure. The lack of electron density for Tyr75 established that this residue was conformationally mobile, even in the enzyme-inhibitor complex. Therefore, the enzyme-inhibitor structure not only demonstrated a new location for the flap and Tyr75, but also established the conformational mobility of these structural features. The significance of this mobility and its implications for inhibitor design, however, went unrecognized.

Additional aspartic peptidase-inhibitor structures have revealed other conformational changes in or near the active site, these conformation changes heretofore having unrecognized implications for inhibitor design. Endothiapepsin, a fungal aspartic peptidase, has been utilized as a model aspartic peptidase system with more than 20 X-ray structures solved for both native and endothiapepsin-inhibitor complexes. The crystallographic evidence suggests endothiapepsin exists in a delicate equilibrium between two observable forms that have considerable differences in active site topography. The two forms are believed to interconvert as a result of environmental conditions, with a rigid body movement largely affecting the $S_3$ binding pocket. The two different conformations are selectively stabilized by inhibitor binding in the $S_3$ subsite. This structural flexibility has also been identified in other aspartic peptidases. Abad-Zapatero et al. (1990) *Proteins: Struct., Funct., Genet.* 8:62.

Development of Peptide-Derived Therapeutic Aspartic Peptidase Inhibitors:

Renin: The aspartic peptidase renin plays a pivotal role in the biosynthesis of the potent vasoconstrictor angiotensin II and inhibitors of this enzyme have been sought for 40 years as potential antihypertensive drugs. Historically, renin inhibitors were developed by replacing the dipeptidyl cleavage site of substrate sequences with an appropriate TSA before any structural data were available to guide structure-based design. Only more recently have a few X-ray structures of renin-inhibitor complexes been solved. While many substrate-derived renin inhibitors showed promise in vitro, none were successfully developed into antihypertensive drugs due to the poor pharmacokinetic properties associated with these peptide-derived inhibitors. However, the principles established in the renin studies facilitated the discovery of HIV protease inhibitors. Most of the known TSAs (Table 1) were first developed for inhibition of renin.

HIV Protease: The most intensely studied aspartic peptidase during the last 200 years is HIV protease, the aspartic peptidase needed for viral replication implicated in AIDS. A variety of peptide-derived peptidomimetic inhibitors of HIV protease have been successfully developed. Numerous X-ray structures of inhibitors bound to HIV protease have been obtained and the structural information has played a central role in the successful development of AIDS drugs.

The first crystal structures of inhibitors bound to HIV protease were the reduced amide analog MVT-101 and the hydroxyethylamine analog, JG-365. MVT-101 lacked the critical hydroxyl group of a TSA inhibitor, but clearly illuminated the $S_3$-$S_3'$ binding sites accessed by the peptidyl inhibitor in the expected extended β-strand binding conformation. The crystal structure of JG-365, a 200-fold more potent inhibitor, bound to HIV protease provided a high resolution view of the critical TSA hydroxyl group interaction with the protease catalytic machinery.

The information gained from both co-crystal structures was immediately utilized in structure-based design processes leading to the currently available AIDS drugs. Both JG-365 and Ro 31-8959 (marketed under the trademark "Saquinavir") were developed as analogs of the Phe-Pro substrate cleavage site:

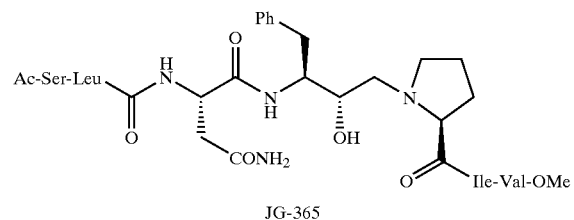

JG-365

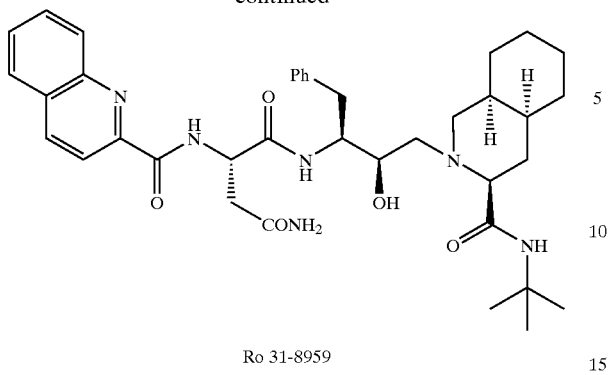

Ro 31-8959

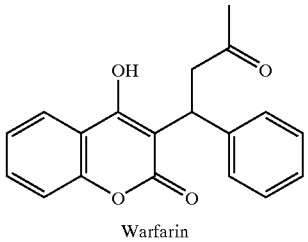

Warfarin

117

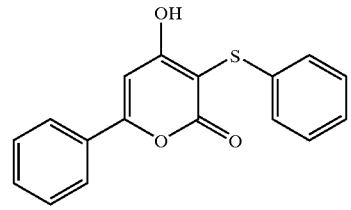

118

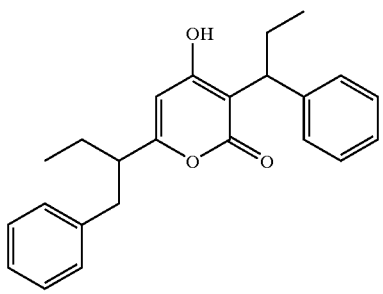

Surprisingly, the hydroxyl group stereochemistry of these potent HIV protease inhibitors is reversed: JG-365 contains an (S) hydroxyl group, while Ro 31-8959 contains an (R) hydroxyl group. Molecular modeling led to the hypothesis that the two diastereomeric peptides adopted different binding modes at the C-terminus of the binding site. This model was confirmed by the X-ray crystal structures of the diastereomeric inhibitors bound to HIV protease. Rich et al. (1991). *J. Med. Chem.* 34:1222–1225.

Changes in flap position and geometry have also been demonstrated for HIV protease. The X-ray structure of Ro 31-8959 bound to HIV protease revealed a new enzyme conformation with an altered flap conformation. This stabilization produced a larger $S_1$ binding site relative to JG-365. Babine & Bender (1997) *Chem. Rev.* 97:1359–1472.

Non-peptide Peptidomimetic Aspartic Peptidase Inhibitors

Very few non-peptide peptidomimetic aspartic peptidase inhibitors have been reported in the literature. Most were obtained by applying structure-based design methods to compounds identified via HTS methods.

The 7-membered cyclic urea HIV protease inhibitors were designed to stabilize the normal extended β-strand binding enzyme conformation, but also to displace a second water molecule stabilizing the enzyme flaps. Lam et al. (1996) *J. Med. Chem.* 39:3514–3525.

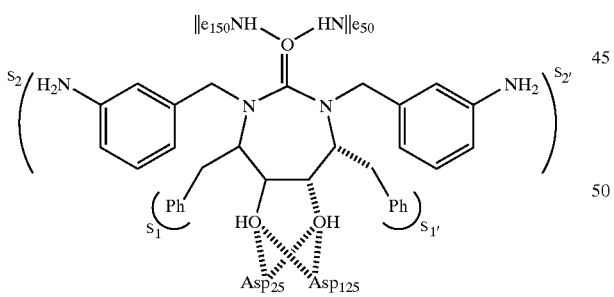

A potential pharmacophore was designed, DeLucca et al. (1997) *Drug Discov. Today* 2: 6–18, and then virtual screening of the HIV active site in the extended β-strand binding conformation with water displaced led to a non-peptide lead structure which was further modified. Inspection of the resulting enzyme-inhibitor crystal structure clearly demonstrates the inhibitor is a non-peptide peptidomimetic that stabilizes the normal extended β-strand binding enzyme conformation.

Discovery efforts at Parke-Davis and Pharmacia simultaneously and independently developed the related pyrone-based HIV protease inhibitors (117 and 118), Tait et al. (1997) *J. Med. Chem.* 40:3781–3792; Turner et al. (1998) *J. Med. Chem.* 41:3467–3476:

Both groups applied structure-based design methods to the anticoagulant Warfarin, identified as an HIV protease inhibitor via HTS. Conversion of the lead compounds into clinically useful drugs was achievable only after high-resolution enzyme-inhibitor crystal structures were obtained. Subsequent optimization eventually afforded the clinically useful HIV protease inhibitors 119 and 120:

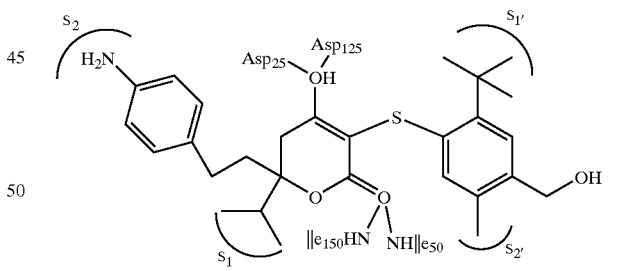

119

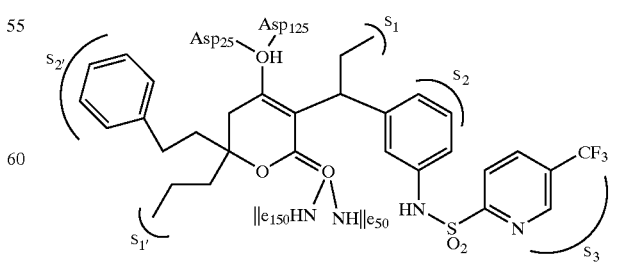

120

Surprisingly, enzyme-inhibitor crystal structures demonstrated that the optimized inhibitors bind in opposite directions, but both stabilize the standard peptide-derived β-strand binding enzyme topography.

Recently, researchers at Roche discovered a series of novel non-peptide inhibitors of renin that bind to a new enzyme active site conformation. Oefner et al. (1999) *Chem. Biol.* 6:127–131; Guller et al. (1999) *Bioorg. Med. Chem. Lett.* 9:1403–1408; Vieira et al. (1999) *Bioorg. Med. Chem. Lett.* 9:1397–1402; and Marki et al. (2001) *Il Farmaco* 56:21–27:

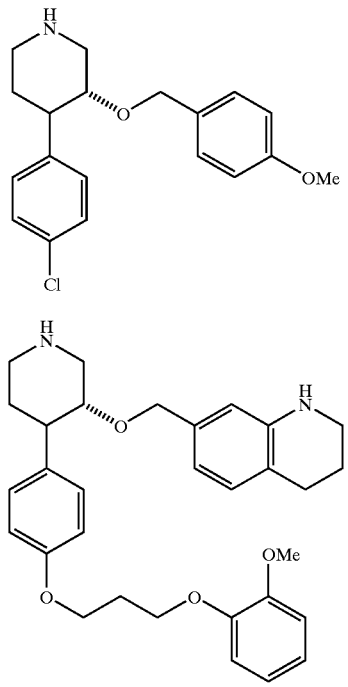

The 3,4-disubstituted piperidines, 4 and 5, inhibit human renin at low micromolar and nanomolar concentrations respectively. More notably, however, these inhibitors stabilize an enzyme active site other than the previously accessed β-strand binding enzyme conformation.

Portions of both lead structure 21 and optimized analog 22 bind in the active site of human renin in a mechanism-based fashion. The binding of the piperidine nitrogen to the enzyme catalytic carboxyl groups is similar to the binding of the statine hydroxyl and aminostatine nitrogen in peptide-derived inhibitors. In addition, the 3-alkoxy group resides in the contiguous $S_1$–$S_3$ enzyme subsite near the normal binding location of the side chains in peptide-derived inhibitors. Piperidines 4 and 5 clearly are non-peptide peptidomimetic inhibitors that stabilize an enzyme conformation not previously observed for this enzyme.

In these complexes, the aspartic peptidase flap structure is stabilized in an open conformation and the Tyr75 side chain is rotated by 120° from its position in the native enzyme, similar to the conformations noted herein with other aspartic peptidases. The stabilization of the open flap with concomitant Tyr75 rotation disrupts a conserved hydrogen bond between Tyr75 and Trp39 believed to be important for keeping the flap closed during catalysis. The breaking of this conserved hydrogen bond allowed the Trp39 side chain to rotate from its usually observed position within one hydrophobic environment into another local hydrophobic environment. This Trp39 side chain rotation opened access to another previously unobserved hydrophobic pocket into which the piperidine 4-phenyl 4'substituent bonded.

Comparison of the active site topography of the enzymes stabilized by peptide-derived and piperidine-derived inhibitors shows a fundamental difference in topographies. The piperidines bind to an enzyme active site that is significantly different from the β-strand binding enzyme conformation. Rotation of Tyr75 destroys much of the binding surface comprising the $S_1$ subsite. Consequently, the peptide-derived inhibitors would not adequately stabilize this conformation within the ensemble. In contrast, the piperidine-derived inhibitors are effective stabilizers of this enzyme form because the piperidine 4-phenyl substituent binds into the space previously occupied by the Tyr75 aromatic ring to regenerate an aromatic cluster. The binding of the 4-phenylpiperidines to the enzyme extended β-strand binding-site is precluded by the superposition of the 4-phenyl group with the Tyr75 aromatic group. Thus, Tyr75 is acting as a "gate keeper," determining which type of inhibitor can bind. In the observed native enzyme conformation and the enzyme conformation stabilized by peptide-derived inhibitors, the piperidines cannot bind; in the alternate piperidine-binding mode, substrate-derived inhibitors cannot bind.

In short, the present inventors have recognized that the piperidine inhibitors stabilize an enzyme conformation not seen in the ensembles stabilized by all inhibitors designed to emulate the β-strand binding-mode. Consequently, the piperidine inhibitors constitute a new class of non-peptide peptidomimetics. What is striking is the close proximity of the piperidine C4 phenyl group to the space vacated by the rotation of Tyr75 in the enzyme. In effect, the piperidine phenyl group has replaced the Tyr75 aromatic ring. This stabilization process, wherein a group from the ligand takes the place of a group in the receptor, is designated herein as "group replacement."

Side chain group replacement has not been used to design peptidase inhibitors, but has been used to design peptidase substrates. In 1987, Wells and coworkers described substrate-assisted catalysis using serine peptidases to illustrate the concept. Carter & Wells (1987) *Science* 237:394–399. Site-directed mutagenesis to remove the active site histidine from subtilisn rendered the mutant enzyme catalytically inactive. But catalytic activity was regained when an imidazole group was placed in a synthetic substrate at a point designed to replace the missing enzyme imidazole group. The mutated enzyme could not cleave normal substrate sequences, but did cleave the designed histidine-containing substrate. The substrate imidazole group replaced the enzyme imidazole group when the substrate was bound to the mutant subtilisn. As noted above, the 4-phenyl groups of the piperidine inhibitors (4 and 5) occupy the space vacated by rotation of Tyr75. More precisely, the piperidine phenyl group replaces the vacated residue to assist the piperidine-stabilization of the enzyme complex.

Extending Empirical Data to Target Novel Conformations:

In the present invention, novel conformations of the binding site are modeled by first modeling the receptor when occupied by a peptide or non-peptide ligand and then altering the model in mechanistically-plausible fashion to arrive at novel conformations of the binding site. These novel conformations are then utilized to design, rationally, new drugs to fit within these novel conformations.

In short, the rational design of non-peptide peptidomimetic inhibitors from the crystal structure of an enzyme-bound peptide-derived peptidomimetic is possible using computer modeling. The evolution of the subject method provides the foundation for rational design of novel non-peptide peptidomimetic inhibitors targeting enzyme conformational ensembles based upon the wealth of existing structural information generated via peptide-like enzyme-inhibitors. A key aspect of the present method is that it examines not the observable bound-receptor conformations, but novel receptor conformations that can be "seen," that is modeled, in silico. Thus, the present invention designs structurally and fundamentally novel inhibitors for a given receptor target by modeling, altering, and analyzing receptor conformations located outside the narrow window of the conformational ensembles presently exploited with peptide-derived inhibitors, and designing peptide or non-peptide peptidomimetics accordingly.

Automated Identification of Novel Inhibitors Based on Novel Conformational Ensembles:

As evidenced by the Examples herein, the present inventors have developed a method to generate fundamentally novel inhibitors by targeting novel receptor conformational ensembles. This method is distinct from the prior art analysis where known structures are docked into known active site conformers. The method thus significantly expands the number of enzyme conformers in the conformational ensemble beyond the numbers now generated to model, for example, the extended β-strand binding site. For example, allowing the mobile flap in an aspartic peptidase to open in 0.1 Å increments would add an estimated 40 sets of additional conformers to the ensemble, each containing some number of active site conformers complementary to a new (for example) heterocyclic scaffold. Further, when using the "GrowMol" program to model potential inhibitors, the inventors have found that inhibitor structures were best generated from active sites stabilized by non-optimal peptide-derived inhibitors. While not being limited to any particular mechanistic explanation for this observation, the assumption is that this occurs because the active sites are not "shrink wrapped" about the inhibitors. Quite clearly, making additional alterations to the active site will yield vastly expanded sets of additional and novel conformers for analysis. Calculating potential scaffolds for each of the potential conformations is, quite clearly, a massive calculation requiring equally massive computation power. But the task is not beyond the power of modern computing equipment. Thus, the present invention will greatly increase the number of non-peptide structures that could serve as scaffolds for inhibitor design and optimization.

Thus, the present method is, by necessity, computationally intensive. One initial concern is the probability that new structures exist that haven't already been evaluated by existing approaches. Bohacek and McMartin, however, have calculated that the number of possible small molecules with molecular weights below 500 is greater than $10^{62}$! Bohacek, McMartin & Guida (1996) *Med. Res. Rev.* 16:3–50. This truly immense number is roughly $10^{52}$ times greater than the now-known organic compounds in this molecular weight range. Thus, to date, the potential conformational space for novel ligands has hardly been probed. It is of course impossible to synthesize all these compounds; there is not enough starting material in the universe. Rich et al., in *Medicinal Chemistry into the Millennium*; Campbell, M. M., Blagbrough, I. S., Eds.; Royal Society of Chemistry, Publ.: Cambridge UK, 2001; pp 16–24. Fortunately it isn't necessary to synthesize even a tiny fraction of all of the compounds possible. After roughly 100 years of the modern pharmaceutical era, there are perhaps only 1000 small-molecule drugs culled from about 10 billion small organic molecules now known. Thus, there is no need to make all organic structures to find new, better drugs.

However, the present invention solves a very long-felt need in drug discovery: to design improved structures that satisfy the necessary goals of inhibiting the target receptor in vivo by modeling small-molecule, non-peptide inhibitors. Today, one of the major stumbling blocks in drug discovery remains identifying orally-active inhibitors. Insofar as peptide-based drugs generally are not orally active, the present method at least partially addresses this problem by generating information on small-molecule, non-peptide inhibitors, inhibitors that are more likely to be orally active than peptide-based inhibitors. Interfacing the present structure-generating method with traditional medicinal chemistry inhibitor design will help focus the many combinatorial synthetic methods on more promising low-molecular weight, non-peptide drug-like structures.

As noted above there are a number of different molecular modeling programs that can be used in the practice of the present invention. The presently available programs generally exploit one of two distinct approaches to generating molecular structures complementary to a given, three-dimensionally and chemically-defined space: "placement-connection" strategies or "fragment-growth" strategies. Both methods utilize high-resolution receptor structures and evaluation programs to rank generated structures for their ability to bind to the defined target. The placement-connection type of ligand-generation program places molecular fragments complementary to the binding site into the receptor binding site. Goodfod, P. J. (1985) *J.Med. Chem.* 28:849; Tomioka & Itai (1994) *J. Comput.-Aided Mol. Des.* 8:347–366. The fragments themselves are drawn from a designated, pre-fabricated fragment library. These types of programs then utilize other programs to connect the fragments in chemically rational relationships. See, for example, Lauri & Bartlett (1994) "CAVEAT: a program to facilitate the design of organic molecules," J. Comput.-Aided Mol. Des. 8:51–66; Eisen et al. (1994) "HOOK: A program for finding novel molecular architectures that satisfy the chemical and steric requirements of a macromolecule binding site," *Proteins: Struct., Funct., Genet.* 19:199–221; Bohm (1992) "LUDI: rule-based automatic design of new substituents for enzyme inhibitor leads," *J. Comp.-Aided Mol. Des.* 6:593–606; Bohm (1992) "The computer program LUDI: a new method for the de novo design of enzyme inhibitors," *J. Comp.-Aided Mol. Des.* 6:61–78; Tschinke & Cohen (1993) "The NEWLEAD program: a new method for the design of candidate structures from pharmacophoric hypotheses," *J. Med. Chem.* 36:3863–3870; and Ho & Marshall (1993) "SPLICE: a program to assemble partial query solutions from three-dimensional database searches into novel ligands," *J. Comput.-Aided Mol. Des.* 7:623–647.

While these types of programs are perfectly acceptable for use in the present invention, they are not preferred. This is because the major disadvantage of the placement-connection approach is that the novelty of the structures generated is necessarily limited by the size of the fragment library used by the program. In short, the program simply cannot construct a novel compound unless the necessary fragments (and logic to connect those fragments) are found within the program.

A second type of ligand-growth program utilizes the fragment-growth method to generate sub-structures from a ligand already bound to the receptor by connecting designated fragments. See Gillet et al. (1995) "SPROUT, HIPPO and CAESA: tools for de novo structure generation and estimation of synthetic accessibility," *Perspect. Drug Discovery Des.* 3:34–50; Moon & Howe (1991) "Computer design of bioactive molecules: a method for receptor-based de novo ligand design," *Proteins* 11:314–328; Rotstein & Murcko (1993) "GroupBuild: a fragment-based method for de novo drug design," *J. Med. Chem.* 36:1700–1710; and Singh, Saldanha, & Thornton (1991) "A novel method for the modeling of peptide ligands to their receptors," *Protein Eng.* 4:251–261. This allows a wide variety of interactions to be generated as the program grows novel inhibitors into the active site. The fragments, however, still come from a defined fragment library, which again limits the potential for structural diversity.

To overcome this limitation, ligand-generating programs that grow structures via single atom growth units are preferred for use in the subject invention. The "GrowMol" program, the preferred program for use in the subject invention, is one such program. These programs are capable of generating novel inhibitors with the greatest amount of molecular interactions and structural diversity. They are also the most computationally intensive of the structure generating programs and require accurate and fast methods to evaluate generated structures. The single atom ligand-growth programs include "LEGEND" (Nishibata & Itai (1991) *Tetrahedron* 47:8985–8990), "GenStar" (Rotstein & Murcko (1993) *J. Comput.-Aided Mol. Des.* 7:23–43), and "GrowMol." An automated design methodology to identify fundamentally novel potential inhibitors can be based upon single atom growth-programs. Considerable computation power, however, is required to handle the multiple novel enzyme active site conformations in the ensemble.

A second embodiment of the present invention locates conformationally mobile residues within the binding site and then identifies potential group replacement peptidomimetics that can fill the voids created by movement of the conformationally mobile residues. This approach is generally referred to herein as "merged group binding." The great advantage of this approach is that it involves a reversal of the normal docking strategy: rather than building a ligand to fit into a defined receptor site, the merged group binding approach docks the enzyme around an inhibitor that is generated within the active site. In this embodiment, after first constructing the desired scaffold model within the active site, potential growth points are identified; i.e. growth points being locations on the ligand that interact with the receptor. These growth points are visible on the model, but appear "blocked" by enzyme groups. By use of the group replacement peptidomimetic concept, potential movable groups within the receptor are identified. A corresponding functionality is then added to a growth point on the potential inhibitor, so that the added functionality overlays the movable enzyme residue. When the movable residue ultimately moves, the added functionality fills the resultant void, thereby stabilizing the altered conformation. This aproach thus provides a method to search for novel inhibitors with the potential to bind altered enzyme conformations. Enzyme docking and minimization experiments applying "Flo" (other Monte Carlo search programs might provide similar results) to the merged enzyme-inhibitor structure quickly identified new side chain arrangements complementary to the merged inhibitor structure. The implementation of these types of searches offers a rational and straightforward method for medicinal chemists to design novel ligands targeting altered conformations within the ensemble.

The Examples that follow reveal that piperidine renin inhibitors are a "peptidomimetic Rosetta Stone" that establishes a logical connection between peptide-derived and non-peptide derived inhibitors of aspartic peptidases. The structural pathway connecting these two classes of peptidomimetics has been revealed by analyzing plausible conformational changes that must occur during proteolysis. Tyr75 was identified as the "Gate Keeper" residue and the mobility of Leu73 and Trp39 also were utilized to generate new binding sites not visible in the crystal structures of either the native or inhibitor-bound enzymes. "Gate Keeper" residues in other enzyme systems can be identified using the same approach.

Non-peptidepeptidomimetics breaking from the extended β-strand conformational mold provide the potential to design smaller, more conformationally constrained molecules. These types of inhibitors have inherent advantages as compared to large, less constrained molecules. For example, the penalties of conformational entropy are "prepaid" during synthesis of novel cyclic scaffolds that are specifically designed to stabilize the receptor active site, as opposed to a more flexible scaffolds that adopt the required conformation only upon binding. The group replacement concept is also favorable from a thermodynamic perspective. And finally hydrophobic interactions can be optimized between ligand and receptor, with the preferred conformation and stereochemistry built directly into a more rigid scaffold.

Using the aspartic peptidases, the inventors have described the conformational mobility observable in enzyme-inhibitor X-ray structures and shown how these examples provide the basis for designing ligands with other protein-ligand systems. For the design of fundamentally novel inhibitors based upon novel receptor conformations, the use of a computer-automation strategy that utilizes single-atom structure generating and ligand evaluation programs has been shown capable of "re-discovering" known inhibitors.

The implementation of the design strategy presented herein may become a new paradigm for the design of medicinally useful organic structures in the $21^{st}$ century. While the present inventors have focused on aspartic peptidases, literature precedent strongly indicates that this strategy will be useful for designing inhibitors of other biological systems.

The new design strategy described herein may also help to identify small molecules that regulate protein-protein interactions. Wells and co-workers, for example, have shown that human growth hormone-receptor interactions are dominated by a relatively small number of critical residues, residues designated as "hot spots" in the receptor. Clackson & Wells (1995) *Science* 267:383–386. Small conformational changes in "hot spot" residues in some receptor systems and subsequent application of the "group replacement" strategy might lead to useful non-peptide peptidomimetics functioning at that receptor. Indeed, designing inhibitors of protein-protein interactions has been a long and often unfruitful process. The method described herein, however, might provide new avenues of future research in this area.

It is even possible these strategies may find use for developing inhibitors of G-protein coupled receptors (GPCR). Using high resolution NMR experiments in conjunction with molecular modeling-based conformational calculations, Inooka and coworkers determined the conformational states of the peptide hormone pituitary adenylate cyclase activating polypeptide (PACAP) when bond to the G-coupled protein PACAP-specific hormone receptor. Inooka et al. (2001) *Nature Structural Biology* 8:161–165. They detected a two-step ligand-binding process in which PACAP first binds nonspecifically to the membrane to promote a shift of the ligand conformational ensemble in its N-terminal region. This shift allows for specific binding to the PACAP receptor. The binding sites of GPCR contain many more amino acid side chains than peptidase active sites, and potentially offer many more productive conformations for ligand binding. Structural data for GPCR are not available today, but once gathered, it is possible to calculate ensembles of potential binding sites for systems this complex using the present invention.

Until now a rational mechanism for transforming peptide-derived peptidomimetics into non-peptide peptidomimetics has not been evident. The present invention, however, targets conformational transitions associated with enzyme catalysis to guide rational design of non-peptide peptidomimetics. Structure-generating programs can facilitate this process by probing the steric constraints within an active site in order to identify enzyme groups with potentially important mobility, and by generating diverse arrays of molecules from which medicinal chemists can extract suitable potential lead structures for further evaluation and synthesis. "GrowMol"-like programs represent a combinatorial design process that can best be exploited when coupled with powerful synthetic methods for optimization. Focused combinatorial synthesis of molecular scaffolds is likely to be a particularly effective way to optimize lead structures into tight-binding, biologically-active inhibitors. The combinatorial design of ligands targeting novel conformational ensembles, coupled with combinatorial synthesis, will lead to the discovery of important new classes of therapeutically useful molecules.

EXAMPLES

Compounds 1 through 5 are known HV protease inhibitors that were developed via high-throughput screening. All of these compounds are considered "non-peptide peptidomimetics" because of their remote structural similarity to peptide substrates. However, X-ray crystal structures of HIV protease complexed with 1, 2, or 3, revealed that the inhibited active site topography is very similar to the inhibited active site topography in HIV protease/peptide complexes.

Known HIV Protease Inhibitors

1

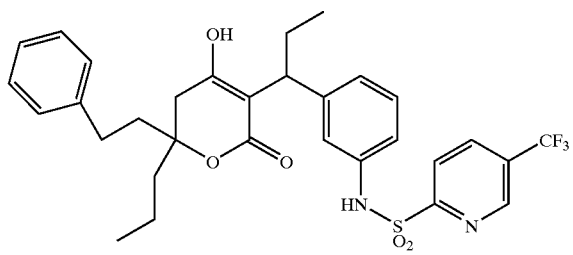

2

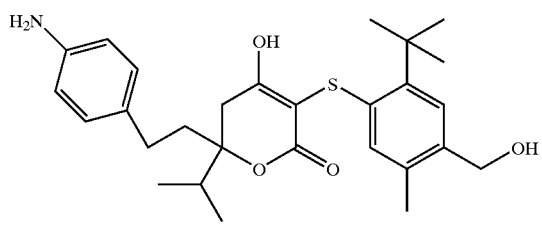

3

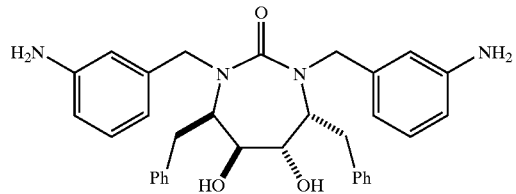

4

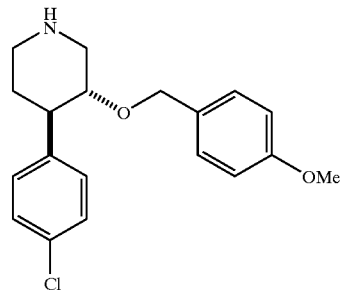

5

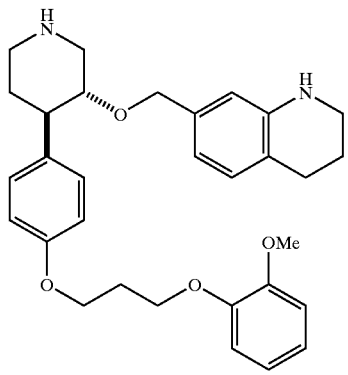

In this Example, the computer program "GrowMol," a molecular modeling program, was used to identify known non-peptide peptidomimetics that bind to a structurally distinct aspartic peptidase active site conformation. The conformation was a nonextended β-strand conformation.

Piperidine 4 inhibits renin at about 26 $\mu$M, while the optimized piperidine inhibitor 5 inhibits renin at low nM concentrations. See Oefner et al. (1996) Chem. Biol. 6:127; Viera et al. (1999) Bioorg. Med. Chem. Let. 9:1397; and Guller et al. (1999) Bioorg Med. Chem. Let. 9:1403. The discovery of these piperidines as a new class of aspartic peptidase inhibitor represents a major advance in the design of inhibitors because these compounds are simple and contain no amide bonds. Moreover, portions of both compounds 4 and 5 bind in the active site of human renin asmechanism-based inhibitors. The binding of the piperidine nitrogen to the enzyme catalytic carboxyl groups is similar to the binding of the statine hydroxyl and the aminostatine nitrogen in the peptide-derived inhibitors. In addition, the binding of the 3-alkoxy group in the $S_1$–$S_3$ enzyme sub-site is close to where the $P_1$ side chain of peptide-derived inhibitors bind. However, the topography of the inhibited active site is fundamentally different from the extended β-strand conformational topography. Piperidine 5 thus constitutes a new type of non-peptide peptidomimetic inhibitor.

As noted above, compounds 1–5 are known HIV protease inhibitors. Thus, for this Example, these compounds were used a model system. Using the present method, an attempt was made first to generate these compounds, or closely related compounds, in the mathematically-modeled active sites of pepsin and *Rhizopus chinensis* pepsin, two enzymes known not to be inhibited by the compounds 1 through 5. The experiment began with the X-ray structure of bis-S-benzyl peptide 6 bound to porcine pepsin. An attempt was then made to "grow" the piperidine unit from the $P_1$ S-benzyl side chain. Growth from that point on CySta 7 toward the catalytic carboxyls generated only acyclic amines, such as compound 8:

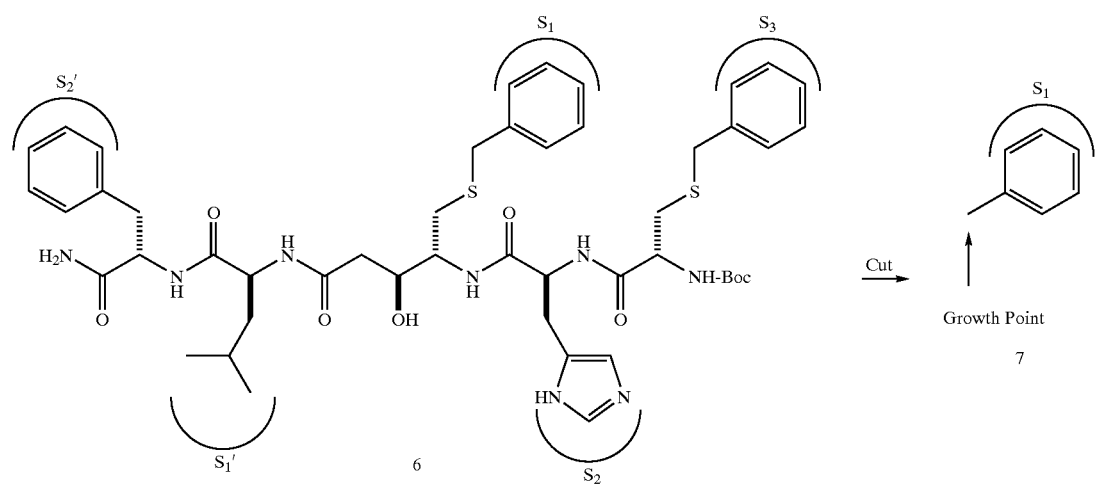

Initial Growth Points Defined by the "GrowMol" Program

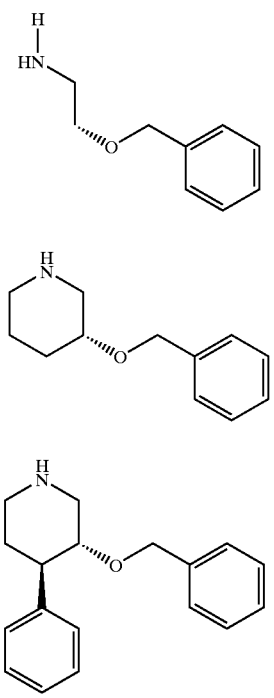

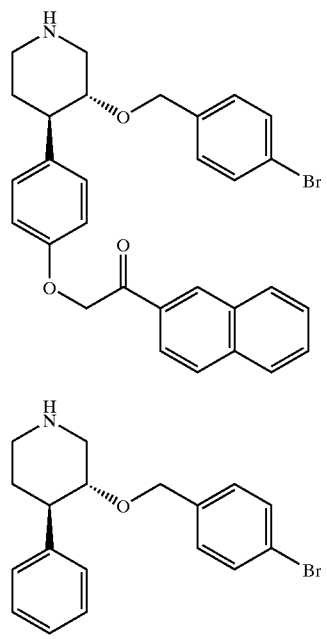

Structures Generated by the "GrowMol" Program

The outcome was that piperidines such as compound 4 could not be generated without altering the active site conformation. This data thus served as a "leaping off" point.

A systematic investigation was then undertaken to determine what other plausible conformations of the binding site will result in binding. In short, the following question was asked: If the compounds known empirically to be protease inhibitors cannot be made to fit into the unaltered conformation of the binding site in the enzyme-substrate complex, would another, chemically- and structurally-plausible conformation result in binding?

Aspartic peptidases are known to contain a hairpin turn structure, or flap region, in the enzyme active site. The flap moves in a hinge motion during peptide inhibitor binding. During inhibitor binding, the end of the flap moves up to 4 Å. Because flap opening is a low-energy process that can occur up to 100 times per second for good substrates, it was decided to "open" this enzyme flap about 1 Å in the mathematical model of the enzyme binding site. With this alteration to the model, the "GrowMol" program generated a series of piperidines such as compound 9, but not the 4-arylpiperidines.

Further examination of the active site by molecular modeling revealed that a −120E rotation of $\chi^1$ in Tyr75 would provide the space needed for growth at C4 of the piperidine system. The change was made to the model and the "GrowMol" program run again. Using this model, the "GrowMol" program generated the 3,4-disubstituted piperidine 10, a direct analog of compound 4. Note that compound 4 was originally identified as a protease inhibitor through high-throughput screening.

In addition, it was previously known that the C4'-position of the 4-phenylpiperidines could be substituted to produce tight-binding renin inhibitors. This tight binding was possible because a tryptophan indole in human renin rotated out of the way to provide an additional binding site for the C4' substituents. Therefore, in the molecular model for pepsin, the Trp39 residue was rotated in the same fashion and the "GrowMol" program run again. With this change to the binding site model, the "GrowMol" program generated acetonaphthone analog compound 11, a compound that is closely related to known inhibitors 4 and 5.

These results show that piperidines 9 and 10 will bind to an active site conformation that is fundamentally different from the extended β-strand topography. Simultaneously, an of critical importance, these results also show that the new active site conformation can be reached via mechanistically related local conformational changes. In other words, not only did the method described herein independently generate compounds empirically shown to be enzyme inhibitors, the conformational changes necessary to result in binding are plausible and well within the scope of conformation dynamics exhibited by macromolecules.

To explore further the compounds generated by running the "GrowMol" program on the altered binding site topography, a new and expedient enantioselective synthesis to prepare piperidine 12 was then developed:

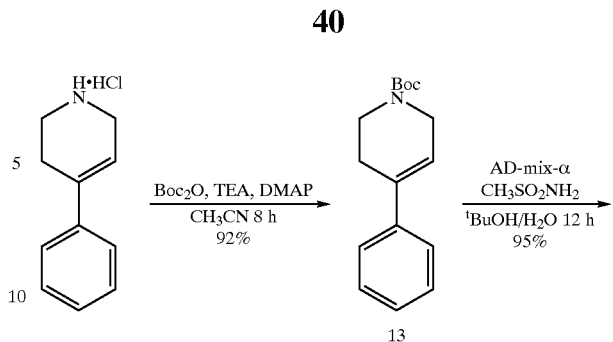

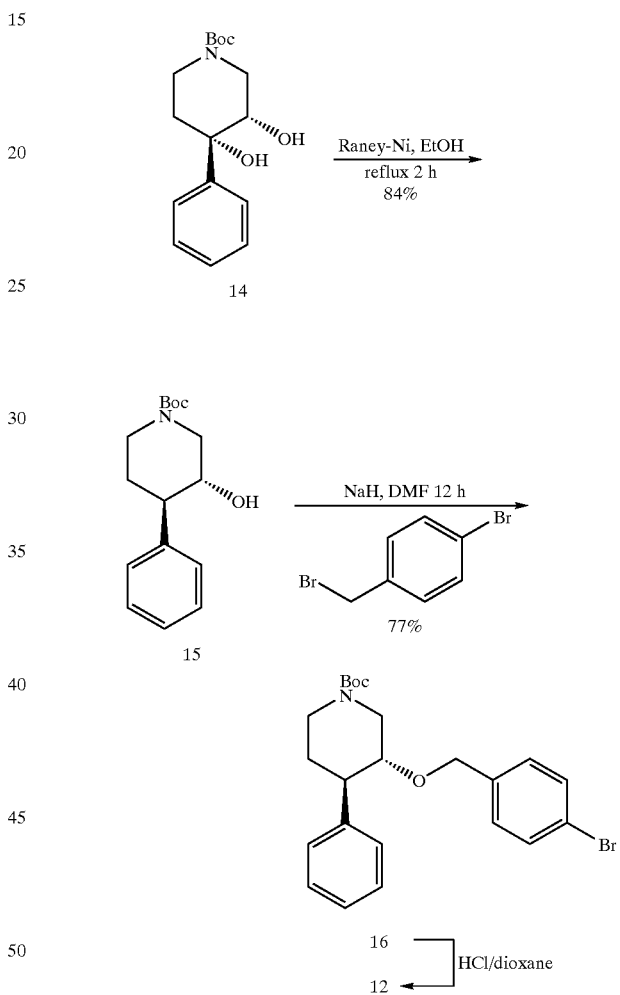

N-protection of 4-phenyl-1,2,3,6-tetrahydropyridine with (N-ert-butoxycabonyl)$_2$O (Boc$_2$O)gave compound 13. Sharpless asymmetric dihydroxylation (AD) was employed to generate the diol 14. Stereoselective reduction of benzylic alcohol 14 with Raney nickel in refluxing EtOH gave compound 15 in >96% enantiomeric excess (ee). The remaining secondary hydroxyl of 15 was alkylated with NaH and p-bromobenzyl bromide in dimethylformamide (DMF) to form the Boc-protected piperidine compound 16. Subsequent removal of the Boc protecting group with HCl-dioxane provided piperidine 12, which was used directly in the enzyme assays.

The enantioselective synthesis of piperidine 11 required slight modifications to the above route:

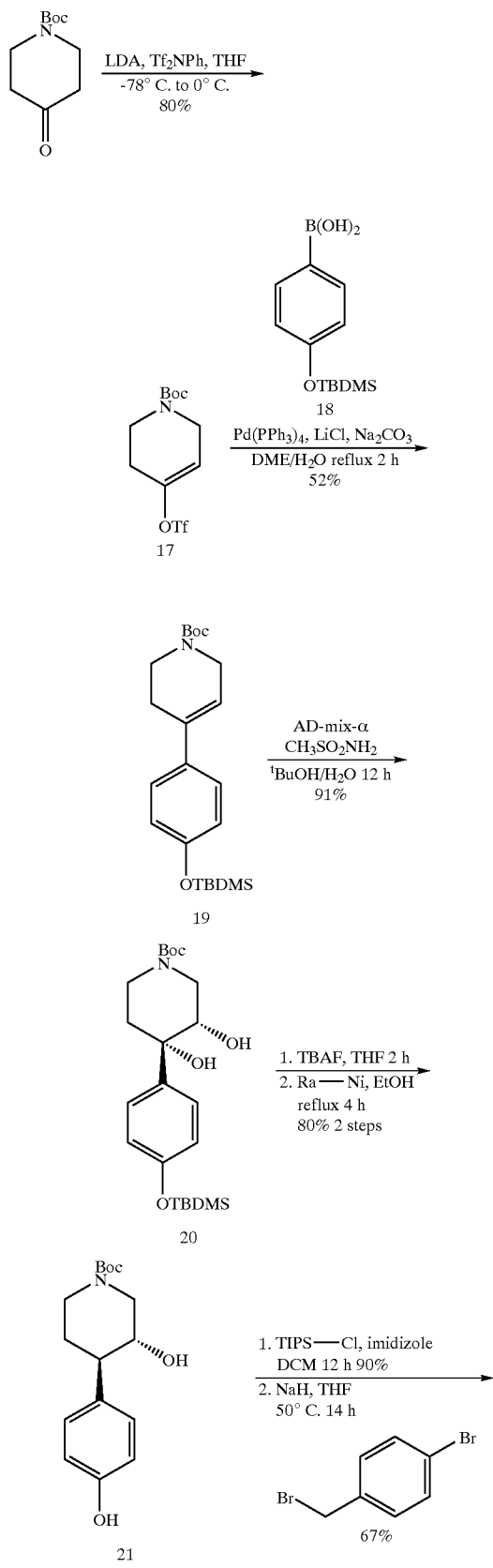

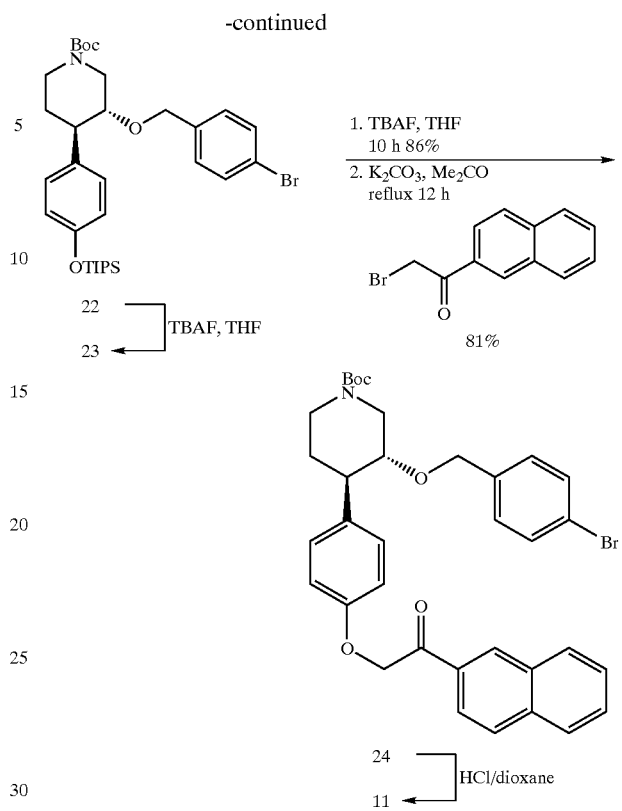

tert-Butyl 4-oxypiperidine-1-carboxylate was converted to the corresponding tetrahydropyridinyl triflate, compound 17, by use of lithium diisopropylamide (LDA) and N-phenyltrifluoromethanesulfonamide. Palladium-mediated coupling of the triflate 17 with the readily prepared arylboronic acid 18 afforded the desired aryltetrahydropyridine 19 in moderate yield. Utilizing Sharpless AD methods, the enantiomerically pure diol 20 was synthesized. However, Raney nickel reduction of the benzylic alcohol in phenol-protected analogs of compound 20 was not successful. After much experimentation, it was determined that the desired Raney nickel reduction of 20 to 21 could be achieved after first removing the silyl-protecting group. Selective protection of the phenol with triisopropylsilyl groups (TIPS), followed by alkylation of the secondary alcohol with NaH and p-bromobenzyl bromide in tetrahyrofuran (THF) provided compound 22. Removal of the TIPS groups with tetrabutylammonium fluoride (TBAF) in THF gave phenol 23, whose stereochemical assignments were confirmed by X-ray structure. Alkylation of compound 23 with potassium carbonate and 2-bromo-2'-acetonaphthone in acetone afforded the desired Boc-protected piperidine, compound 24. Removal of the Boc protecting group with HCl-dioxane provided the piperidine, compound 11, which was used directly in the enzyme assays.

Inhibition of substrate hydrolysis by porcine pepsin and R. chinensis pepsin was determined using prior art assay conditions. See Flentke et al. (1999) Protein Expression Purif. 16:213 and Peranteau et al. (1995) Anal. Biochem. 227:242. Piperidine 11 inhibited porcine pepsin with an $IC_{50}=0.2$ μM.

The results of this Example show that the present invention can be used generate inhibitors of a given enzyme or receptor on a rational basis based upon conformational analysis of the binding site in a receptor-ligand complex. In short, as shown by this Example, the present method is able to generate the structure of non-peptidepeptidomimetics that are closely related structurally to inhibitor compounds found empirically using high-throughput screening methods.

As shown by this Example, to achieve these results, it was necessary to alter the conformation of portions of the enzyme active site. These conformational changes were implemented after careful consideration of plausible enzyme intermediates that could be formed during catalysis. All of the changes made to the model were low-barrier conformational changes.

In short, this Example demonstrates that it is possible to identify non-peptide peptodomimetics utilizing structure modeling programs and the crystal structure of a peptide-derived inhibitor bound to the enzyme. The process described herein represents a novel protocol for altering enzyme active sites to permit design of non-peptide peptidomimetic inhibitors that bind to novel enzyme active site conformers. These results are consistent with recent calculations that show ligands bind to the dynamic ensemble of preexisting enzyme conformations such that binding of an inhibitor selectively stabilizes those conformational states in which the binding site is formed.

This Example also demonstrates a rational approach to peptidomimetic design can include inhibitors designed to stabilize potential preexisting enzyme active site conformations, in addition to those conformations observable in both native and inhibitor-enzyme crystal structures. Rather than design peptidomimetics to emulate only the enzyme-bound conformation of the peptide-derived inhibitor (the extended β-strand topography), as is conventionally done, the method of the present invention targets the complete ensemble of potential preexisting active site conformations.

Thus, structure-generating programs that allow systematic variation of the position of the starting growth points, that permit systematic evaluation of the dynamic ensembles of preexisting enzyme active site conformations, and that provide systematic evaluation (scoring) of the grown structures, will greatly accelerate the discovery of non-peptide peptidomimetic inhibitors.

What is claimed is:

1. A method of generating chemical structures of putative non-peptide inhibitors of a biologically-active receptor, the method comprising:
    (a) constructing a model in silico of a receptor-ligand complex using empirical three-dimensional data of the receptor-ligand complex, the model including a receptor portion and a ligand portion, whereby a conformation of a binding site on the receptor, between the receptor portion of the model and the ligand portion of the model, is revealed; then
    (b) excising the ligand portion from the model of the receptor-ligand complex of step (a), thereby yielding an in silico model of a conformation of a binding site on the receptor absent the ligand; then
    (c) altering the in silico model of the conformation of the binding site absent the ligand of step (b) to yield a model of an altered conformation of the binding site; and then
    (d) generating models of non-peptide chemical structures that are complementary in structure to the altered conformation of the binding site absent the ligand from step (c), whereby chemical structures of putative non-peptide inhibitors of the altered conformation are revealed.

2. The method of claim 1, wherein in step (d), the models of non-peptide chemical structures are generated in silico.

3. The method of claim 1, wherein the empirical three-dimensional data used in step (a) is X-ray crystallographic data.

4. The method of claim 1, wherein the empirical three-dimensional data used in step (a) is nuclear magnetic resonance data.

5. The method of claim 1, wherein the empirical three-dimensional data used in step (a) is X-ray crystallographic data and nuclear magnetic resonance data.

6. The method of claim 1, wherein in step (c), the conformation of the binding site is altered using Monte Carlo methods.

7. The method of claim 1, wherein in step (d), models of the non-peptide chemical structures are generated using a computer molecular modeling program.

8. A method of generating, in silico, chemical structures of putative non-peptide inhibitors of a biologically-active receptor, the method comprising:
    (a) obtaining empirical three-dimensional data of the receptor bonded to a proteinaceous or non-proteinaceous ligand, the receptor and the ligand bonded thereto collectively referred to as a receptor-ligand complex; then
    (b) constructing a model of the receptor-ligand complex in silico using the data from step (a); then
    (c) excising the ligand from the model of the receptor-ligand complex of step (b), thereby yielding an in silica model of a conformation of a binding site on the receptor; then
    (d) altering the model of the conformation of the binding site of step (c) to yield a model of an altered conformation of the binding site; and then
    (e) generating, in silico, models of non-peptide chemical structures that are complementary in structure to the altered conformation of the binding site from step (d), whereby structures of putative non-peptide inhibitors of the altered conformation are revealed.

9. The method of claim 8, wherein the empirical three-dimensional data obtained in step (a) is X-ray crystallographic data.

10. The method of claim 8, wherein the empirical three-dimensional data obtained in step (a) is nuclear magnetic resonance data.

11. The method of claim 8, wherein the empirical three-dimensional data obtained in step (a) is X-ray crystallographic data and nuclear magnetic resonance data.

12. The method of claim 8, wherein in step (d), the conformation of the binding site is altered using Monte Carlo methods.

13. The method of claim 8, wherein in step (e), models of the non-peptide chemical structures are generated using a computer molecular modeling program.

* * * * *